(12) United States Patent
Brady et al.

(10) Patent No.: US 7,588,773 B2
(45) Date of Patent: Sep. 15, 2009

(54) METHODS AND COMPOSITIONS FOR DIAGNOSING AND PREVENTING A GROUP B STREPTOCOCCAL INFECTION

(75) Inventors: Linda Jeannine Brady, Gainesville, FL (US); Kyle N. Seifert, Harrisonburg, VA (US); Elisabeth E. Adderson, Memphis, TN (US); John F. Bohnsack, Salt Lake City, UT (US)

(73) Assignees: St. Jude Children's Research Hospital, Memphis, TN (US); University of Florida, Gainesville, FL (US); University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 11/574,067

(22) PCT Filed: Aug. 19, 2005

(86) PCT No.: PCT/US2005/029521

§ 371 (c)(1),
(2), (4) Date: Jun. 1, 2007

(87) PCT Pub. No.: WO2006/137838

PCT Pub. Date: Dec. 28, 2006

(65) Prior Publication Data

US 2008/0039386 A1    Feb. 14, 2008

Related U.S. Application Data

(60) Provisional application No. 60/604,095, filed on Aug. 24, 2004.

(51) Int. Cl.
*A61K 39/09* (2006.01)
*C07K 14/315* (2006.01)
*C07H 21/04* (2006.01)
*C12P 21/04* (2006.01)
*C12N 15/00* (2006.01)

(52) U.S. Cl. ............... 424/244.1; 424/184.1; 530/350; 435/69.7; 435/320.1; 536/23.7

(58) Field of Classification Search .............. None
See application file for complete search history.

(56) References Cited

U.S. PATENT DOCUMENTS 6,635,473 B1    10/2003    Foster et al.

OTHER PUBLICATIONS

Houghten et al. (Vaccines, 1986, Edited by Fred Brown: Cold Spring Harbor Laboratory.*
Lederman et al (Molecular Immunology 28:1171-1181, 1991.*
Li et al , Proc. Natl. Acad. Sci. USA 77:3211-3214, 1980.*
Pang et al. (Infection and Immunity, vol. 67 No. 4, pp. 1821-1827, 1999).*
Bohnsack et al., "Long-Range Mapping of the *Streptococcus agalactiae* Phylogenetic Lineage Restriction Digest Pattern Type III-3 Reveals Clustering of Virulence Genes", Infection and Immunity 2002 70(1):134-139.
Seifert et al., "Elimination of srr-2 attenuates virulence of Group B Streptococcus", 2003 Gen Meet Am Soc Microbiol 103rd, Washington DC.
Takahashi et al., "Identification of a Highly Encapsulated, Genetically Related Group of Invasive Type III Group B Streptococci", The Journal of Infectious Diseases 1998 177:1116-1119.
NCBI Genbank Accession No. AAF72510 [gi:8101007] with Revision History—May 29, 2000-Jul. 25, 2000.
NCBI Genbank Accession No. T30214 [gi:7470970] with Revision History—Sep. 6, 1995-May 11, 2000.
NCBI Genbank Accession No. S19702 [gi:97813] with Revision History—Jan. 1, 1900-Oct. 15, 1999.

* cited by examiner

*Primary Examiner*—Robert B Mondesi
*Assistant Examiner*—Padma V Baskar
(74) *Attorney, Agent, or Firm*—Licata & Tyrrell P.C.

(57) ABSTRACT

The present invention provides a group B *streptococcal* (GBS) surface antigen, designated epsilon antigen, that is co-expressed with the delta antigen on a subset of serotype III GBS. Epsilon is expressed on more pathogenic Restriction Digest Pattern (RDP) III-3 GBS, but not on RDP types 1, 2, or 4. Accordingly, the present invention provides compositions and methods for detecting a group B *streptococcus* serotype III, RDP III-3 strain. Vaccines and methods of identifying agents which inhibit adhesion of a group B *streptococcal* cell to a host cell are also provided.

2 Claims, No Drawings

METHODS AND COMPOSITIONS FOR DIAGNOSING AND PREVENTING A GROUP B STREPTOCOCCAL INFECTION

INTRODUCTION

This application claims the benefit of priority from U.S. provisional patent application Ser. No. 60/604,095, filed Aug. 24, 2004, the content of which is incorporated herein by reference in its entirety.

This invention was made in the course of research sponsored by the Department of Energy (Grant No. DE-FG09-93ER-20097), National Institute of Dental and Craniofacial Research (Grant No. DE07200), National Institutes of Health (Grant No. P30 CA21765, and National Institute of Allergy and Infectious Diseases (Grant No. AI40918). The U.S. government may have certain rights in this invention.

BACKGROUND OF THE INVENTION

Lancefield group B streptococci (GBS) are a major cause of neonatal sepsis (Baker et al. (1990) Rev. Infect. Dis. 12(Suppl. 4):S463-8) and are important pathogens in adults (Farley (2001) Clin. Infect. Dis. 33(4):556-61). There are two main divisions of neonatal GBS disease, early- and late-onset disease (Baker et al. (1990) supra; Ferrieri (1985) Antibiot. Chemother. 35:211-24) Early-onset disease occurs within the first week of life and is vertically transmitted from mother to infant, with eighty percent of all GBS infections being of this type. All of the known serotypes have been isolated from infants suffering from early-onset disease. Three manifestations of early-onset disease include sepsis with no known focus of infection, meningitis, and pneumonia. Late-onset disease occurs from one week to three months after birth. Serotype III GBS are responsible for approximately 90% of all late-onset infections (Baker et al. (1990) supra), with meningitis being a common clinical manifestation that results in a substantial number of survivors suffering permanent neurological damage. Serotype III organisms are responsible for approximately 90% of all cases of meningitis (Baker et al. (1990) supra), whether or not the meningitis is a result of early- or late-onset disease. Therefore, serotype III GBS are responsible for a substantial portion of GBS disease.

Several surface proteins from group B streptococci have been identified in an attempt to characterize the complex nature of the cell wall and polysaccharide capsule. C-protein was first described using a polyclonal rabbit antiserum made against whole formalin-killed cells of CDC strain A909 (Wilkinson and Eagon (1971) Infect. Immun. 4(5):596-604). Antibodies against group- and serotype-specific carbohydrates in polyclonal rabbit antiserum were eliminated by exhaustive adsorption with a c-protein-negative serotype Ia strain, and the non-serotype Ia antigens that the antiserum bound to were called the c-protein. It was later recognized that c-protein typing serum actually recognizes at least four antigenic moieties, alpha, beta, (Wilkinson and Eagon (1971) supra; Johnson and Ferrieri (1984) J. Clin. Microbiol. 19(4): 506-10; Bevanger (1985) Acta. Pathol. Microbiol. Immunol. Scand. [B] 93(2):113-9) gamma, and delta (Brady et al. (1988) J. Infect. Dis. 158(5):965-72; Chun et al. (1991) J. Infect. Dis. 163(4):786-91). The genes encoding the alpha and beta proteins have been cloned (Cleat and Timmis (1987) Infect. Immun. 55(5):1151-5; Michel et al. (1991) Infect. Immun. 59(6):2023-8) and the encoded proteins characterized. Reactivity of gamma has been found to correspond to a variant amino-terminus of the alpha protein. The nature of the epsilon antigen is unclear, although it is associated with acyl-carrier protein in cell sonicates and SDS extracts of GBS whole cells (Seifert, et al. (2003) Gen. Meet. Am. Soc. Microbiol. 103$^{rd}$, Washington, D.C.). Another antigenic marker, protein Rib (resistance to protease, immunity, group B), which is immunologically distinct from delta, has also been described (Stalhammar-Carlemalm et al. (1993) J. Exp. Med. 177(6):1593-603). The alpha, beta, and gamma antigens are expressed primarily by serotype Ia, Ib, and II organisms, while delta and Rib have been reported to be expressed by most serotype III strains (Brady et al. (1988) supra; Chun et al. (1991) supra; Stalhammar-Carlemalm et al. (1993) supra). Other surface proteins that have been identified include the R and X proteins (Ferrieri (1988) Rev. Infect. Dis. 10(Suppl 2):S363-6), C5a peptidase (Beckmann et al. (2002) Infect. Immun. 70(6):2869-76; Cleary et al. (1992) Infect. Immun. 60(12):5219-23), Sip (Brodeur et al. (2000) Infect. Immun. 68(10):5610-8), Lmb (Spellerberg et al. (1999) Infect. Immun. 67(2):871-8), Fbs, and a Rib-like protein (Areschoug et al. (1999) Infect. Immun. 67(12):6350-7). Collectively, these studies indicate that a variety of molecules, several of unknown function, are present on the surface of GBS and some of these are more commonly detected on strains within a given serotype.

In addition to classifying GBS according to polysaccharide capsule, serotype III GBS isolates can be further classified based on HindIII and Sse83871 restriction digest patterns (RDPs) of chromosomal DNA into four distinct lineages, designated RDP types III-1, -2, -3, and -4 (Takahashi et al. (1998) J. Infect. Dis. 177(4):1116-9). The majority (91%) of serotype III invasive neonatal isolates have been reported to be RDP III-3, suggesting that these strains may represent a more virulent lineage of serotype III GBS. Genomic subtractive hybridization has been used to identify DNA sequences unique to RDP III-3 strains (e.g., clones AA3.8, AA3.14, AA3.16, AA4.1, AA4.13, AW-10, DY-1, DY-3, and DY-11) (Bohnsack et al. (2002) Infect. Immun. 70(1):134-9), however, individual coding sequences within most of these clones have not been identified and characterized as to their contribution to the pathogenicity of RDP III-3 GBS.

SUMMARY OF THE INVENTION

A novel group B *streptococcal* surface antigen has now been identified. This surface antigen is co-expressed with the delta antigen on the same subset of serotype III GBS and has been designated epsilon antigen. The immunologically reactive epsilon glycoprotein has been characterized and is a glycoprotein expressed by the highly pathogenic RDP III-3 lineage. Nucleic acid sequences encoding the epsilon glycoprotein have been isolated and shown to encode a unique serine-rich repeat protein (Srr-2). Thus, epsilon glycoprotein is useful as an immunologic marker for diagnosing group B *streptococcal* infection, for treating group B *streptococcal* infection and as a vaccine against virulent group B *streptococcus*.

Accordingly, the present invention relates to an isolated nucleic acid encoding a serine-rich repeat protein-2 (Srr-2). Said isolated nucleic acid is:

(a) a nucleotide sequence of SEQ ID NO:1;

(b) a nucleotide sequence that hybridizes to a nucleotide sequence of SEQ ID NO:1 or its complementary nucleotide sequence under stringent conditions, wherein said nucleotide sequence encodes a Srr-2;

(c) a nucleotide sequence encoding an amino acid sequence encoded by the nucleotide sequences of (a) or (b), but which has a different nucleotide sequence than the nucleotide sequences of (a) or (b) due to the degeneracy of the genetic code or the presence of non-translated nucleotide sequences; or (d) a portion of a nucleotide sequence of (a), (b), or (c).

The present invention also relates to an isolated Srr-2 or epsilon glycoprotein. In one embodiment, said isolated Srr-2 protein has an amino acid sequence having at least about 70% amino acid sequence similarity to an amino acid sequence of SEQ ID NO:2 or a fragment thereof. In another embodiment, the Srr-2 protein is the glycosylated epsilon antigen.

The present invention further relates to an expression vector containing an isolated nucleic acid encoding an Srr-2 protein and a cultured cell containing said isolated nucleic acid or a protein encoded thereby.

Further provided by the present invention is a composition containing an isolated Srr-2 or epsilon glycoprotein, or an antigenic fragment thereof, and a pharmaceutically acceptable carrier. In one embodiment, said composition is a vaccine.

The present invention further relates to an isolated binding agent which specifically recognizes and binds a group B *streptococcal* epsilon antigen or Srr-2 protein of SEQ ID NO:2. In one embodiment, the binding agent is an antibody. In another embodiment, the binding agent is a peptide aptamer.

Further provided in the instant invention is a method for specifically delivering an active agent to a group B *streptococcus* serotype III, RDP III-3 cell. The method involves administering to a subject having or suspected of having a group B *streptococcus* serotype III, RDP III-3 infection an effective amount of an active agent operably linked to a binding agent which specifically recognizes and binds a group B *streptococcal* epsilon antigen or Srr-2 protein of SEQ ID NO:2 so that the active agent is specifically delivered to a group B *streptococcus* serotype III, RDP III-3 cell in said subject.

The present invention also provides a diagnostic method for detecting group B *streptococcus* serotype III, RDP III-3. In one embodiment, the method involves detecting the epsilon antigen in a sample via contacting the sample with a binding agent which specifically binds an epsilon antigen to form a binding agent-epsilon antigen complex, wherein the presence of such a complex is indicative of the presence of a group B *streptococcus* serotype III, RDP III-3 in the sample. In another embodiment, the method involves detecting a nucleic acid sequence of SEQ ID NO:1 encoding a Srr-2 protein. The nucleic acid sequence encoding the Srr-2 protein can be detected by PCR amplifying at least a portion of said nucleic acid sequence using two or more primers which specifically interact with nucleic acid sequences encoding the Srr-2 protein and detecting said amplified sequence. Alternatively, Srr-2 nucleic acid sequences can be detected by binding to a microarray composed of an oligonucleotide, an aptamer, a cDNA, an antibody, or fragment thereof, which specifically binds to the at least a portion of the nucleic acid sequence encoding epsilon antigen.

Further provided is a kit for identifying the presence of epsilon antigen. Such a kit contains a binding agent which specifically binds a group B *streptococcal* epsilon antigen.

The present invention further provides a method for identifying an agent which blocks adhesion of a group B *streptococcus* serotype III, RDP III-3. The method involves contacting a *streptococcal* cell expressing epsilon antigen with a test agent and measuring the expression or activity of the epsilon antigen as compared to a control. A decrease in the expression or activity of the epsilon antigen is indicative of said agent blocking the adhesion of a group B *streptococcus* serotype III, RDP III-3. Such agents are useful in preventing or treating group B *streptococcus* serotype III, RDP III-3 infection in subjects having or suspected of having such an infection.

DETAILED DESCRIPTION OF THE INVENTION

A novel immunologic marker, designated epsilon antigen (also referred to herein as epsilon glycoprotein), has now been identified which is co-expressed with delta antigen on a subset of serotype III GBS. The reactivity of epsilon antigen was associated with the more pathogenic RDP III-3 lineage and anti-epsilon antigen antibodies react with recombinant Srr-2 cloned from a serotype III, RDP III-3 strain, indicating that the Srr-2 is part of the protein backbone of the epsilon glycoprotein antigen.

Polyclonal rabbit antisera made against a serotype III/delta$^+$ strain (J48) was rendered more highly specific for delta by exhaustive adsorption with the serotype III/delta$^-$ strain DL700. This reagent was subsequently absorbed with GBS strain A909 (serotype Ic/alpha/beta/gamma/delta) (Brady et al. (1988) supra) to remove antibodies against delta. The delta-reactive and A909-absorbed antisera were incubated with a panel of GBS whole cells in a radioimmunoassay. The delta-reactive antiserum reacted with A909 (serotype Ic/alpha/beta/gamma/delta) and a subset of serotype III strains. After adsorbing the delta-specific antiserum with strain A909 (serotype Ic/alpha/beta/gamma/delta), the additionally adsorbed antiserum was not reactive with the absorbing strain A909, but was still reactive with all serotype III strains that expressed the delta antigen. These results indicated that another immunological reactivity was associated with the delta antigen on a subset of serotype III strains and that this antigen was absent from strain A909. This newly identified antigen was designated epsilon antigen and the anti-J48 antiserum that had been exhaustively adsorbed with both strains DL700 and A909 was used as the epsilon-specific antiserum in subsequent experiments. Over 30 serotype III/delta-positive strains were tested and found to express epsilon antigen. No serotype III strain was identified which expressed epsilon antigen in the absence of delta antigen, or vice versa.

In addition to immunological classification of serotype III GBS into two groups based on the presence or absence of the delta and epsilon antigens, serotype III GBS can be subdivided into four distinct lineages based on HindIII and Sse83871 restriction digest patterns (RDPs) of chromosomal DNA (Takahashi, et al. (1998) supra). Representative strains of RDP III types 1, 2, 3, and 4 were assayed for epsilon antigen expression by whole cell ELISA (Table 1) to determine if there was a correlation between delta/epsilon antigen-expression and RDP type.

TABLE 1

| RDP Type | Number of Strains Tested | Number of Strains Positive for Epsilon Expression[a] | % Positive |
|---|---|---|---|
| III-1 | 2 | 0 | 0 |
| III-2 | 15 | 0 | 0 |
| III-3 | 15 | 15 | 100 |
| III-4 | 3 | 0 | 0 |

[a]Strains were determined to be positive for epsilon antigen expression as described Examples.

RDP strains 1, 2, or 4 tested negative for epsilon antigen expression, while all fifteen RDP III-3 strains tested were epsilon antigen-positive. Subsequent molecular typing of three serotype III/delta/epsilon-positive strains (J48, J52, and PEH) and two serotype III/delta/epsilon-negative strains (DL700, DL1104) revealed that the former strains were RDP III-3 strains, while the latter strains were non-III-3. The majority (91%) of serotype III invasive neonatal isolates have been reported to be RDP III-3 (Takahashi, et al. (1998) supra). It has also been shown that serotype III GBS isolated from septic sources appeared to exhibit a higher frequency of expression of delta/epsilon (83.3%, n=18) compared to serotype III isolates from colonizing sources (58.8, n=34), although the sample size was too small to ascertain statistical significance. Taken together, these results indicate that delta/epsilon expression by serotype III GBS is an antigenic marker for the RDP III-3 lineage.

The art has suggested that RDP III-3, delta/epsilon-positive GBS comprise a more pathogenic lineage of serotype III GBS (Takahashi et al. (1998) supra; Brady, et al. (1996) supra). In addition, a high virulence clone of type III *S. agalactiae* has been reported to cause invasive neonatal disease (Musser, et al. (1989) *Proc. Natl. Acad. Sci. USA* 86(12): 4731-5) and is now known to correspond to the RDP III-3 lineage (Fleming, et al. (2004) *J. Med. Micro.* 53:505-8). The RDP III-3 lineage referred to herein is identified as the sequence type 17 complex (Bohnsack et al., (2003) *J. Clin. Microbiol.* 41:2530-6). Therefore, $LD_{90}$ experiments were conducted to evaluate potential differences in lethality of representative strains in a neonatal mouse model (Rodewald, et al. (1992) *J. Infect. Dis.* 166(3):635-9). Four delta/epsilon-positive serotype III strains (874391, COH1, J52, and J48) and four delta/epsilon-negative serotype III strains (DL700, DL785, 865043, and ATCC12403) were tested. $LD_{90}$ values partitioned into two distinct groups based on the presence or absence of the delta/epsilon antigen. RDP III-3, delta/epsilon-positive strains had $LD_{90}$ values between $4.6 \times 10^2$ and $8 \times 10^3$ cfu (colony-forming units), while delta/epsilon-negative strains demonstrated significantly higher values between $9.8 \times 10^6$ and $6 \times 10^8$ cfu ($p<0.0005$). This large difference in $LD_{90}$ values between the two subsets of serotype III strains indicated that delta/epsilon-positive RDP III-3 organisms are more virulent than other serotype III GBS strains.

To isolate and characterize the ε antigen, sonic extracts of strain J48 (serotype III/delta/epsilon) and delta/epsilon-negative GBS strain DL700 (serotype III) were prepared and subjected to anion-exchange chromatography in parallel. The polyclonal anti-epsilon antigen antiserum used specifically to detect epsilon antigen on the surface of GBS whole cells recognized additional antigens in whole cellular extracts. Therefore, a competition ELISA was used to identify epsilon antigen in individual anion-exchange column fractions. Material contained in fractions 13-17 (eluted from the column with 0.2 M NaCl) from J48 (serotype III/delta/epsilon) inhibited anti-epsilon antigen antiserum binding to J48 whole cells to a greater degree than other column fractions from J48 or any column fraction from DL700 (serotype III). This indicated that epsilon antigen was contained in these column fractions. These fractions also contained other surface antigens such as delta antigen and serotype III polysaccharides, identified by competition ELISA and western immunoblot analysis, and the group B carbohydrate, identified by latex agglutination. Material from a J48 column fraction 14 contained epsilon antigen, as determined by competition ELISA, was separated on a 7.5% SDS-polyacrylamide gel, transferred to a nitrocellulose membrane, and incubated with anti-epsilon antigen antiserum to identify immunoreactive bands present in the J48 sample, compared with the corresponding column fraction from DL700 (serotype III). A prominent band migrating at >250-kDa was reactive with anti-epsilon antigen antiserum and present only in the column fraction from J48. This material could not be stained with COO-MASSIE® or silver stain, a characteristic of highly anionic glycoproteins. This material was subsequently eluted from an SDS-gel slice and shown to inhibit anti-epsilon antigen binding to J48 whole cells by competition ELISA, confirming that the high molecular weight material contained the epsilon antigen.

To determine whether the epsilon antigen was sensitive to proteolysis, J48 whole cells were treated with proteinase K. The ability of anti-epsilon antigen antiserum to react with proteinase K-treated J48 cells was substantially reduced, indicating that epsilon antigen is a protein-containing antigen. To further characterize the epsilon antigen, J48 (serotype III/delta/epsilon) whole cells were treated with sodium metaperiodate. Treatment of J48 (serotype III/delta/epsilon) whole cells with sodium metaperiodate reduced anti-epsilon antigen binding by over 50% compared to buffer-only-treated whole cells, indicating that carbohydrate was also a component of the epsilon antigen. Reactivity of anti-epsilon antigen antibodies to the >250-kDa protein band identified as epsilon antigen by western immunoblot analysis was also eliminated by proteinase K or sodium metaperiodate treatment, confirming the results observed with GBS whole cells and further indicating that epsilon antigen is a glycoprotein antigen.

Since epsilon antigen reactivity was localized by western immunoblot analysis to just above the 250-kDa protein standard on SDS-PAGE, epsilon antigen-containing material from J48 (serotype III/delta-epsilon) and the corresponding high-molecular weight material from DL700 (serotype III) was eluted from this region of SDS-polyacrylamide gels. The extracted materials were analyzed by western immunoblot, wherein duplicate membranes were incubated with polyclonal anti-delta antigen, anti-epsilon antigen, and anti-serotype III antiserum. Anti-epsilon antigen antiserum reacted with high molecular weight material in the sonic extract from J48 (serotype III/delta/epsilon), but not from strain DL700 (serotype III). Anti-epsilon antigen antibodies reacted with the >250-kDa material eluted from an SDS-polyacrylamide gel of the sonic extract of strain J48, but not DL700. Neither anti-delta antigen nor anti-serotype III antisera reacted with the >250-kDa gel-purified material from either strain. The >250-kDa gel-purified material from both strains was also tested for the presence of the group B carbohydrate by latex agglutination. Material recovered from both strains contained group B, but not groups A, C, D, or G carbohydrate as determined by latex agglutination. The gel-purified material from strain J48, containing both epsilon antigen and group B carbohydrate and DL700 containing group B carbohydrate was subjected to carbohydrate composition analysis. Material from both J48 and DL700 contained rhamnose, mannose, galactose, and glucose in a molar ratio of 4:1:1:6. Amino acid analysis of the same preparations also indicated the presence of either a glycine- or serine-rich protein.

Genomic subtractive hybridization has been used to identify DNA sequences unique to RDP III-3 strains (Bohnsack et al. (2002) supra). One clone, designated DY-3, was derived from GBS strain 874391 and contained a 3,618 bp open reading frame (srr-2, serine-rich repeat 2) that was predicted to encode an unusual high molecular weight protein (125 kDa) with a highly repetitive serine—(36%) and aspartate—(12%) rich carboxyl terminal region. The predicted protein (Srr-2) contained a signal peptide and Leu-Pro-Xaa-Thr-Gly (SEQ ID NO:3) cell wall-anchor domain (Fischetti, et al. (1990) *Mol. Microbiol.* 4(9):1603-5). It had only limited similarity to a serine-rich protein present in both the GBS RDP III-1 strain NEM316 and serotype V strain 2603V/R genomes (Glaser, et al. (2002) *Mol. Microbiol.* 45(6):1499-513; Tettelin, et al. (2002) *Proc. Natl. Acad. Sci. U.S.A.*

99(19):12391-6). The nucleic acid sequence of this open reading frame (SEQ ID NO:1) was not homologous to any sequence in the GENBANK database. To determine if the protein encoded by srr-2 contained in clone DY-3 represented a protein component of the epsilon antigen, the srr-2 open reading frame amplified by PCR from J48 (serotype III/delta/epsilon) was cloned into a pBAD-TOPO® (INVITROGEN™) expression vector and expression of Srr-2 was induced in *E. coli*. *E. coli* lysates were assayed by western immunoblot for the presence of the recombinant protein using a monoclonal antibody directed against the V5 epitope portion of the expressed fusion protein. A reactive band was detected at >250 kDa. The recombinant Srr was also reactive with anti-epsilon antigen antiserum by western immunoblot analysis. The apparent molecular mass of >250 kDa was bigger than the size predicted for the recombinant Srr (125 kDa); however, when the protein was analyzed under strong denaturation conditions of 9 M urea, migration of Srr-2 was as predicted. This indicated that Srr-2 may have migrated as a dimer when urea was absent from the gel. The reactivity of recombinant Srr-2 with anti-epsilon antigen antibodies indicated that the Srr-2 protein from J48 is a component of the epsilon antigen. Reactivity of anti-epsilon antigen antibodies with J48 whole cells was diminished but not completely destroyed by treatment of whole cells with sodium metaperiodate. Treatment of whole cells with proteinase K virtually eliminated anti-epsilon antigen reactivity. Collectively, these results indicate that Srr-2 is the protein backbone of the epsilon glycoprotein antigen.

The predicted amino acid sequence of srr-2 (SEQ ID NO:2) had limited similarity to the predicted serine-rich protein (Srr-1) observed in both the GBS RDP III-1 strain NEM316 (19.8% identity) and serotype V strain 2603V/R (18.2% identity) genomes (Glaser, et al. (2002) supra; Tettelin, et al. (2002) supra). Srr-1 from these strains share identical non-repeat region primary sequence but differ by 400 nucleotides in the length of the long repeat region (RII) sequence. The predicted amino acid sequence of Srr-2 from RDP III-3 strains J48 and 874391 were nearly identical except that the RII region from 874391 strain contained an additional 100 amino acid residues. Each Srr variant is relatively large, with approximately a 50-amino acid residue signal sequence, a small N-terminal serine-rich repeat region located between two non-repeat regions, a large serine-rich repeat region (RII) that comprises a substantial portion of the entire protein, and a cell wall-anchor domain near the C-terminus. The amino acids that alternate with serine in the repeat regions of most Srr proteins vary among individual proteins. The overall predicted secondary structure of the Srr proteins from GBS is similar to that of serine-rich repeat proteins from other *streptococcal* species (Bensing, {Bensing, et al. (2002) *Mol. Microbiol.* 44(4):1081-94; Takahashi, et al. (2002)_*Infect. Immun.* 70(3):1209-18; Wu, et al. (1999) *Mol. Microbiol.* 34(5):1070-81). Therefore, representative GBS strains were tested to determine the relationship between epsilon antigen expression and the presence of either serine-rich repeat open reading frames (srr-1 or srr-2) by Southern hybridization. It was found that a DIG-labeled srr-1 PCR product amplified from DL700 (serotype III, RDP III-1) genomic DNA hybridized with all epsilon antigen-negative strains, while all epsilon antigen-positive strains hybridized with the srr-2 PCR product amplified from J48 (serotype III/delta/epsilon, RDP III-3) genomic DNA. This demonstrated that only RDP III-3 strains possess srr-2. Conversely, non-RDP III-3 strains that do not express delta/epsilon, possess srr-1.

As demonstrated herein, delta/epsilon-positive serotype III GBS strains did not possess the srr-1 open reading frame present in the NEM316 genome. The srr-1 open reading frame is located in a putative operon similar to that of a locus in *S. gordonii* named secY2-A2 because of the presence of additional secA and secY homologues dedicated to the export of GspB, a Srr-1 homologue (Bensing, et al. (2002) supra). To determine whether srr-2 from strain J48 was located in a similar secY2/A2 locus, genes located upstream and downstream of srr-2 were sequenced and analyzed for the presence of open reading frames. The homology of translated amino acid sequences was compared to that of other proteins entered into the GENBANK database using the BLASTp analysis program. In strain J48, a secY2 gene homologue was located immediately downstream of srr-2, and followed by asp1-3, secA2, gtf, gtfB, nss, and gly gene homologues similar to those that encompass the secY2/A2 loci of other *streptococcal* and *staphylococcal* species (Takamatsu, et al. (2004) *Mol. Microbiol.* 52(1):189-203). The srr-2-containing locus of J48 also has an organization more similar to *staphylococcal* species than other *streptococcal* species (Takamatsu, et al. (2004) supra) in that the secY2 gene lies only 113 nucleotides downstream of the srr-2 gene, whereas NEM316 srr-1 and secY2 are separated by approximately 12-kb of DNA that includes nss, gly, and putative glycosyltransferases genes, and the nss and gly genes are located at the 3' end of the locus.

The Srr glycoproteins from *S. parasanguis* and *S. gordonii* have been characterized as adhesins. Fap1 from *S. parasanguis* binds to saliva-coated hydroxyapatite (Wu, et al. (1999) supra; Wu, et al. (1998) *Mol. Microbiol.* 28(3):487-500), while *S. gordonii* GspB mediates binding to human platelets (Bensing and Sullam (2002) *Mol. Microbiol.* 44(4):1081-94). *S. gordonii* show a significant decrease in its ability to bind to human platelets when GspB is not surface-localized (Bensing and Sullam (2002) supra). Similarly, Fap1 expression is essential for *S. parasanguis* to bind to saliva-coated hydroxyapatite (Wu, et al. (1999) supra; Wu, et al. (1998) supra). *S. gordonii* DL1 contains a gene with a deduced amino acid similar to that reported for GspB. This protein, Hsa, mediates binding to alpha2-3-linked sialoglycoconjugates and bacterium-mediated hemagglutinating activity (Takahashi, et al. (2002) supra). The deduced amino acid sequence of the central region of Srr-2 has similarity to fibrinogen binding proteins of *Staphylococcus aureus* (GENBANK Accession No. S19702) and *S. epidermidis* (GENBANK Accession No. T30214 and AAF72510). Therefore, it is contemplated that Srr-2 is an adhesin and useful in vaccines to serotype III, RDP III-3 GBS.

Accordingly, the present invention relates to nucleic acid sequences encoding Srr-2, Srr-2 protein, epsilon glycoprotein, binding agents which specifically bind Srr-2 protein or epsilon glycoprotein and methods for using the same in diagnosis of a GBS infection, vaccines against GBS and for identifying agents which block adhesion of a GBS such as serotype III, RDP III-3.

Thus, the present invention is an isolated nucleic acid containing a nucleotide sequence encoding a serine-rich repeat 2 (Srr-2) protein. As used herein, an isolated molecule (e.g., an isolated nucleic acid such as genomic DNA, RNA or cDNA or an isolated polypeptide) means a molecule separated or substantially free from at least some of the other components of the naturally occurring organism, such as for example, the cell structural components or other polypeptides or nucleic acids commonly found associated with the molecule. When the isolated molecule is a polypeptide, said polypeptide is at least about 25%, 50%, 60%, 70%, 75%, 80%, 85%, 90%, 95%, 97%, 98%, 99% or more pure (w/w).

In one embodiment, the nucleotide sequence encoding an Srr-2 protein is a nucleotide sequence of SEQ ID NO:1. In another embodiment, the nucleotide sequence encoding an Srr-2 protein is a nucleotide sequence that hybridizes to a nucleotide sequence of SEQ ID NO:1 or its complementary nucleotide sequence under stringent conditions. In a further embodiment, the nucleotide sequence encoding an Srr-2 protein is a nucleotide sequence encoding an Srr-2 protein but which has a different nucleotide sequence than the nucleotide sequences of SEQ ID NO:1 due to the degeneracy of the genetic code or the presence of non-translated nucleotide sequences (e.g., 5' or 3' untranslated regions). Further, fragments or portions of any of the above nucleotide sequences are also considered embodiments of the present invention.

In the identification of a nucleotide sequence of the present invention, hybridization of a nucleotide sequence to a nucleotide sequence of SEQ ID NO:1 can be carried out under conditions of reduced stringency, medium stringency or even stringent conditions (e.g., conditions represented by a wash stringency of 35-40% Formamide with 5×Denhardt's solution, 0.5% SDS and 1×SSPE at 37° C.; conditions represented by a wash stringency of 40-45% Formamide with 5× Denhardt's solution, 0.5% SDS, and 1×SSPE at 42° C.; and/or conditions represented by a wash stringency of 50% Formamide with 5× Denhardt's solution, 0.5% SDS and 1×SSPE at 42° C., respectively) to the sequences disclosed herein. See, e.g., Sambrook et al., *Molecular Cloning, A Laboratory Manual* (2d Ed. 1989) (Cold Spring Harbor Laboratory).

Alternatively stated, isolated nucleic acids encoding Srr-2 of the invention have at least about 60%, 70%, 80%, 90%, 95%, 97%, 98% or higher sequence similarity with the isolated nucleic acid sequences disclosed herein (or fragments thereof) and encode an Srr-2 protein or epsilon antigen as defined herein.

It will be appreciated by those skilled in the art that there can be variability in the nucleic acids that encode the Srr-2 protein of the present invention due to the degeneracy of the genetic code. The degeneracy of the genetic code, which allows different nucleic acid sequences to code for the same polypeptide, is well-known in the literature (see Table 2).

TABLE 2

| Amino Acid | 3-Letter Code | 1-Letter Code | Codons |
|---|---|---|---|
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC ACT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

Further variation in the nucleic acid sequence can be introduced by the presence (or absence) of non-translated sequences, such as 5'- and 3'-untranslated sequences.

Moreover, the isolated nucleic acids of the invention encompass those nucleic acids encoding Srr-2 proteins that have at least about 70%, 80%, 90%, 95%, 97%, 98% or higher amino acid sequence similarity with the protein sequences specifically disclosed herein (or fragments thereof) and further encode a epsilon protein as defined herein.

As is known in the art, a number of different programs can be used to determine whether a nucleic acid or polypeptide has sequence identity or similarity to a known sequence. Sequence identity and/or similarity can be determined using standard techniques known in the art, including, but not limited to, the local sequence identity algorithm of Smith & Waterman (1981) *Adv. Appl. Math.* 2:482, by the sequence identity alignment algorithm of Needleman & Wunsch (1970) *J. Mol. Biol.* 48:443, by the search for similarity method of Pearson & Lipman (1988) *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux, et al. (1984) *Nucl. Acid Res.* 12:387-395, either using the default settings, or by inspection.

An example of a useful algorithm is gapped BLAST as reported by Altschul, et al. (1997) *Nucleic Acids Res.* 25:3389-3402.

A percentage amino acid sequence identity value can be determined by the number of matching identical residues divided by the total number of residues of the longer sequence in the aligned region. The longer sequence is the one having the most actual residues in the aligned region (gaps introduced by WU-Blast-2 to maximize the alignment score are ignored).

The alignment can include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the shorter sequence in the aligned region and multiplying by 100. The longer sequence is the one having the most actual residues in the aligned region.

To modify Srr-2 amino acid sequences specifically disclosed herein, amino acid substitutions can be based on any characteristic known in the art, including the relative similarity or differences of the amino acid side-chain substituents, for example, their hydrophobicity, hydrophilicity, charge, size, and the like. In particular embodiments, conservative substitutions (i.e., substitution with an amino acid residue having similar properties) are made in the amino acid sequence encoding Srr-2.

In making amino acid substitutions, the hydropathic index of amino acids may be considered. The importance of the hydropathic amino acid index in conferring interactive biologic function on a protein is generally understood in the art (see, Kyte and Doolittle (1982) *J. Mol. Biol.* 157:105). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle (1982) supra), and these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is also understood in the art that the substitution of amino acids can be made on the basis of hydrophilicity. U.S. Pat. No. 4,554,101 teaches that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Isolated nucleic acids of this invention include RNA, DNA (including cDNAs) and chimeras thereof. The isolated nucleic acids can further contain modified nucleotides or nucleotide analogs. Fragments or portions of the nucleotide sequences of the present invention can be 10, 20, 30, 40, 40 or more nucleotides of the sequences disclosed herein. For example, a fragment of a nucleotide sequence of the present invention can encode for a truncated epsilon antigen.

As used herein, the term protein is used interchangeably with polypeptide and is intended to encompass peptides and antigenic fragments, unless indicated otherwise.

While Srr-2 protein and epsilon antigen can be biochemically distinguished as one is glycosylated (i.e., epsilon antigen) and the other lacks glycosylation (i.e., Srr-2), when referring to the protein backbone of SEQ ID NO:2, Srr-2 protein and epsilon antigen are encoded by the same nucleic acid sequence and therefore have the same primary amino acid sequence. Thus, truncations and modifications of the Srr-2 amino acid sequence are applicable to the amino acid sequence of epsilon antigen. An Srr-2 protein also includes modified Srr-2 (e.g., mutated to alter glycosylation sites), Srr-2 fragments such as truncated molecules (e.g., antigenic fragments for antibody production or vaccines) and Srr-2 fusion proteins (e.g., an Srr-2-GST protein fusion or Srr-2-His tagged protein to facilitate purification).

An epsilon antigen or Srr-2 protein of SEQ ID NO:2 for use in antibody production, in vitro assays or for vaccines can be isolated using various methods. For example, an epsilon antigen can be recombinantly-produced, chemically-synthesized, or isolated from group B *streptococcal* cells.

As will be appreciated by one of skill in the art, a full-length Srr-2 protein or epsilon antigen or epsilon glycoprotein can be produced or isolated for use in accordance with the invention, however, fragments of an Srr-2 protein or epsilon antigen can also be used provided the fragment maintains the desired activity of the full-length protein or is an antigenic fragment of Srr-2 protein or epsilon antigen. Antigenic fragments can be determined experimentally or empirically using such programs as EMBOSS's Antigenic and GCG's PeptideStructure and PlotStructure. For example, it is contemplated that, similar to truncated GspB constructs lacking the C-terminal wall anchor (Bensing, et al. (2004) *J. Bacteriol.* 186:638-45), truncation of Srr-2 protein lacking wall anchor sequences will result a secreted form of the epsilon antigen. Moreover, it is contemplated that the non-repetitive portion of the Srr-2 protein or epsilon antigen is the functional part and that the repetitive portion acts as a scaffold to display the functional domain extracellularly at some distance from the bacterial cell wall. Thus, a fragment of a Srr-2 protein or epsilon antigen can encompass the functional domain.

As used herein, a protein or fragment that maintains the desired activity of the full-length protein (i.e., a functional protein, peptide, or fragment) is one that retains at least one biological activity normally associated with that protein (e.g., enhancing adhesion to a host cell). Alternatively, a functional protein or fragment retains all of the activities possessed by the unmodified protein. By retains biological activity, it is meant that the protein retains at least about 50%, 60%, 75%, 85%, 90%, 95%, 97%, 98%, 99%, or more, of the biological activity of the native protein (and can even have a higher level of activity than the native protein). A non-functional protein is one that exhibits essentially no detectable biological activity normally associated with the protein (e.g., at most, only an insignificant amount, e.g., less than about 10% or even 5%).

In general, recombinant production of an Srr-2 protein requires incorporation of nucleic acid sequences encoding said protein (e.g., SEQ ID NO:1) into a recombinant expression vector in a form suitable for expression of the protein in a recombinant host cell.

A suitable form for expression provides that the recombinant expression vector includes one or more regulatory sequences operatively-linked to a nucleic acid sequence encoding an Srr-2 protein in a manner which allows for transcription of the nucleic acids into mRNA and translation of the mRNA into the protein. Regulatory sequences can include promoters, enhancers and other expression control elements (e.g., polyadenylation signals). Such regulatory sequences are known to those skilled in the art and are described in Goeddel D. D., ed., Gene Expression Technology, Academic Press, San Diego, Calif. (1991). It should be understood that the design of the expression vector can depend on such factors as the choice of the recombinant host cell to be transfected and/or the level of expression required. Nucleic acid sequences or expression vectors harboring nucleic acid sequences encoding an Srr-2 protein can be introduced into a recombinant host cell, which can be of eukaryotic or prokaryotic origin by standard techniques for transforming cells. Suitable methods for transforming recombinant host cells are found in Sambrook, et al. (Molecular Cloning: A Laboratory Manual, 3rd Edition, Cold Spring Harbor Laboratory Press (2000)) and other laboratory manuals. The number of recombinant host cells transformed with a nucleic acid sequence encoding an Srr-2 protein will depend, at least in part, upon the type of recombinant expression vector used and the type of transformation technique used. Nucleic acids can be introduced into a recombinant host cell transiently, or more typically, for long-term expression of an Srr-2 protein, the nucleic acid sequence is stably integrated into the genome of the recombinant host cell or remains as a stable episome in the recombinant host cell. Once produced, an Srr-2 protein can be recovered from culture medium as a secreted polypeptide, although it also can be recovered from host cell lysates or cellular debris when directly expressed without a secretory signal. When an Srr-2 protein is expressed in a recombinant host cell other than one of *streptococcal* origin (e.g., *e. coli*, fungi such as *Saccharomyces cerevisiae* or *Shizosaccharomyces pombe*, or animals such as mice or bovine), said protein is substantially free of proteins or polypeptides of *streptococcal* origin. However, it may be necessary to purify the protein from recombinant host cell proteins or polypeptides using conventional protein purification methods to obtain preparations that are substantially homogeneous as to an Srr-2 protein. As a first step, the culture medium or lysate is centrifuged to separate particulate cell debris. The membrane and soluble protein fractions are then separated. The recombinant protein can then be purified from the desired fraction. The recombinant protein thereafter is purified from contaminant soluble proteins and polypeptides using any of the following suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; or gel filtration using, for example, SEPHADEX G-75.

Of particular interest is recombinant overexpression and isolation of Srr-2 from a *streptococcal* cell capable of producing an ε antigen with the native post-translational modifications (i.e., glycosylation). Suitable expression vectors and *streptococcal* cells for expressing an ε antigen are well-known within the art (see, for example, Byrd, et al. (2002) *Vaccine* 20(17-18):2197-205). Suitable Streptococcal cells for expressing an epsilon antigen include those of the group B streptococci and are advantageously serotype III, RDP III-3.

In addition to recombinant production, an Srr-2 protein can be produced by direct peptide synthesis using solid-phase techniques (Merrifield (1963) *J. Am. Chem. Soc.* 85:2149-2154). Protein synthesis can be performed using manual techniques or by automation. Automated synthesis can be achieved, for example, using Applied Biosystems 431A Peptide Synthesizer (Perkin Elmer, Boston, Mass.). Various fragments of an Srr-2 protein can be chemically-synthesized separately and combined using chemical methods to produce a full-length molecule.

Alternatively, an epsilon antigen can be isolated from its natural source, a group B *streptococcus* serotype III, RDP III-3 cell. Using the method exemplified herein or any art-established method for isolating proteins to homogeneity, an epsilon antigen can be isolated for use in antibody production, in vitro assays or for vaccines. An antibody specific for the epsilon antigen can subsequently be used for affinity purification of the epsilon antigen.

The present invention further relates to an isolated binding agent which specifically recognizes and binds to a group B *streptococcal* epsilon antigen or Srr-2 protein of SEQ ID NO:2. Such a binding agent can bind to and be specific for an Srr-2 protein and/or epsilon antigen by binding the carbohydrate and/or protein component of the Srr-2 protein and/or epsilon antigen. Binding agents are intended to include antibodies as well as peptide aptamers.

Peptide aptamers which specifically bind to an Srr-2 protein and/or epsilon antigen can be rationally designed or screened for in a library of aptamers (e.g., provided by Aptanomics SA, Lyon, France). In general, peptide aptamers are synthetic recognition molecules whose design is based on the structure of antibodies. Peptide aptamers consist of a variable peptide loop attached at both ends to a protein scaffold. This double structural constraint greatly increases the binding affinity of the peptide aptamer to levels comparable to that of an antibody (nanomolar range). Likewise, aptamers which bind to nucleic acid sequences encoding epsilon antigen, can also be identified in library screens.

Antibodies to an Srr-2 protein and/or epsilon antigen of the invention can be generated using methods that are well-known in the art. Such antibodies can include, but are not limited to, polyclonal, monoclonal, chimeric, single chain, Fab fragments, and fragments produced by a Fab expression library. Neutralizing antibodies are especially desirable for therapeutic use.

For the production of antibodies, various hosts including goats, rabbits, rats, mice, humans, and others, may be immunized by injection with an Srr-2 protein or epsilon antigen or any fragment or oligopeptide thereof which has antigenic or immunogenic properties. Depending on the host species, various adjuvants can be used to increase the immunological response. Such adjuvants include, but are not limited to, Freund's, mineral gels such as aluminum hydroxide, and surface-active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially suitable.

When oligopeptides, peptides, or fragments of Srr-2 protein or epsilon antigen are used for the production of antibodies, generally they have an amino acid sequence consisting of at least five amino acids and more desirably at least 10 amino acids. Fragments of epsilon antigen can be generated by, for example, tryptic digestion and extraction from a preparative SDS-PAGE gel. Likewise, fragments of an Srr-2 protein can be generated by digestion or by recombinant fragment expression and purification. Further, an Srr-2 protein or epsilon antigen, or antigenic fragment thereof, can be glycosylated as it is found in its native state or it can lack glycosylation. However, as the carbohydrate component is believed to be involved in the adhesion activity of the epsilon antigen, it may be desirable to use a glycosylated epsilon antigen for producing an antibody. Further, short stretches of amino acids of an epsilon antigen of the invention can be fused with those of another protein such as keyhole limpet hemocyanin and antibody produced against the chimeric molecule.

Monoclonal antibodies to an epsilon antigen of the invention can be prepared using any technique that provides for the production of antibody molecules by continuous cell lines in culture. These include, but are not limited to, the hybridoma technique, the human B-cell hybridoma technique, and the EBV-hybridoma technique (Kohler, et al. (1975) *Nature* 256: 495-497; Kozbor, et al. (1985) *J. Immunol. Methods* 81:31-42; Cote, et al. (1983) *Proc. Natl. Acad. Sci.* 80:2026-2030; Cole, et al. (1984) *Mol. Cell. Biol.* 62:109-120).

In addition, techniques developed for the production of humanized and chimeric antibodies, the splicing of mouse antibody genes to human antibody genes to obtain a molecule with appropriate antigen specificity and biological activity, can be used (Morrison, et al. (1984) *Proc. Natl. Acad. Sci.* 81, 6851-6855; Neuberger, et al. (1984) *Nature* 312:604-608; Takeda, et al. (1985) *Nature* 314:452-454). Alternatively, techniques described for the production of single chain antibodies can be adapted, using methods known in the art, to produce specific single chain antibodies. Antibodies with related specificity, but of distinct idiotypic composition, can be generated by chain shuffling from random combinatorial immunoglobulin libraries (Burton (1991) *Proc. Natl. Acad. Sci.* 88,11120-11123).

Antibodies can also be produced by inducing in vivo production in the lymphocyte population or by screening immunoglobulin libraries or panels of highly specific binding reagents as is well-known in the art (Orlandi, et al. (1989) *Proc. Natl. Acad. Sci.* 86: 3833-3837; Winter, et al. (1991) *Nature* 349:293-299).

Antibody fragments, which contain specific binding sites for an Srr-2 protein and/or epsilon antigen, or a fragment thereof, can also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries can be constructed to allow rapid and easy identification of monoclonal Fab fragments with the desired specificity (Huse, et al. (1989) *Science* 254:1275-1281).

Diabodies are also contemplated. A diabody refers to an engineered antibody construct prepared by isolating the binding domains (both heavy and light chain) of a binding antibody, and supplying a linking moiety which joins or operably links the heavy and light chains on the same polypeptide chain thereby preserving the binding function (see, Holliger et al. (1993) *Proc. Natl. Acad. Sci. USA* 90:6444; Poljak (1994) *Structure* 2:1121-1123). This forms, in essence, a radically abbreviated antibody, having only the variable domain necessary for binding the antigen. By using a linker that is too short to allow pairing between the two domains on the same chain, the domains are forced to pair with the complementary domains of another chain and create two antigen-binding sites. These dimeric antibody fragments, or diabodies, are bivalent and bispecific. It should be clear that any method to generate diabodies, as for example described by Holliger, et al. (1993) supra, Poljak (1994) supra, Zhu, et al. (1996) *Biotechnology* 14:192-196, and U.S. Pat. No. 6,492,123, herein incorporated by reference, can be used.

Various immunoassays can be used for screening to identify antibodies, or fragments thereof, having the desired specificity for Srr-2 protein and/or epsilon antigen. Numerous protocols for competitive binding (e.g, ELISA), latex agglutination assays, immunoradiometric assays, and kinetics (e.g. BIACORE™ analysis) using either polyclonal or monoclonal antibodies, or fragments thereof, with established specificity are exemplified herein and are well-known in the art. Such immunoassays typically involve the measurement of complex formation between a specific antibody and its cognate antigen. A two-site, monoclonal-based immunoassay utilizing monoclonal antibodies reactive to two non-interfering epitopes is suitable, but a competitive binding assay can also be employed.

Alternatively, a binding agent can be subjected to other biological activity assays, e.g., bacterial adhesion assays, in order to evaluate its potency or pharmacological activity and potential efficacy as a therapeutic agent. Such assays are well-known in the art.

As epsilon antigen is a surface protein, another embodiment of the present invention relates to the use of a binding agent which interacts with an extracellular portion of the epsilon antigen to specifically deliver an active agent to a group B *streptococcus* serotype III, RDP III-3 cell in a subject having of suspected of having an infection thereof. Such a method is particularly advantageous if the active agent is toxic to the subject, has undesirable side effects, or when the bacterium has evaded the host immune response. Active agents for use in the method of the present invention include those identified in accordance with the screening method disclosed herein as well as other bactericidal agents, bacteriostatic agents, or agents which mark the bacterial cell for destruction by the immune system of the subject. It is contemplated that the active agent can be operably linked to the binding agent via any linkage such as a biodegradable linkage (e.g., a glycine-ester bond or a disulfide bond) or a non-degradable linkage (e.g., an amide bond) depending on whether the active agent is to be taken up by the bacterial cell (i.e., a bactericidal or bacteriostatic agent) or left at the bacterial surface, e.g., when marked for destruction by the immune system. These and other linkers and uses thereof are well-known in the art. Exemplary bactericidal agents which can be delivered to a group B *streptococcus* serotype III, RDP III-3 cell using a binding agent of the invention include, but are not limited to, cefuroxime, penicillin, ampicillin, clindamycin, or erythromycin. Bacteriostatic agents can include, e.g., chloramphenicol. In the case of marking a bacterial cell for destruction, one strategy is to increase the immune response by loading the antibody with antigenic material in the CDR regions (Bona, et al. (1998) *Immunol. Today* 19:126-133). As epsilon antigen is only found in group B *streptococcus* serotype III, RDP III-3 isolates, the present invention provides methods for identifying such isolates in a sample via detecting the presence of nucleic acid sequences encoding Srr-2 and epsilon antigen and protein encoded thereby. In one embodiment of this diagnostic method, the presence of the epsilon antigen is detected in assays using a binding agent that specifically binds to epsilon antigen (e.g, the carbohydrate and/or protein component). In this embodiment, a sample (e.g., an environmental material such as soil or water, a food sample, or a biological fluid such as blood, plasma, sputum, cerebral spinal fluid, amniotic fluid, vaginal/rectal swab and the like) is contacted with a binding agent (e.g., an antibody) which binds epsilon antigen and a resulting antigen-binding agent complex is washed, to remove non-specific binding, and detected using standard assays (e.g., an immunoassay) as exemplified herein. When the binding agent is, for example, a peptide aptamer, the binding agent-antigen complex can be directly detected by, for example, a detectable marker protein (e.g., β-galactosidase, GFP or luciferase) fused to the aptamer. Subsequently, the presence or absence of an epsilon antigen-binding agent complex is correlated with the presence or absence, respectively, of a group B *streptococcus* serotype III, RDP III-3 isolate in the sample. It is contemplated that the sample can be from an individual suspected of having a group B *streptococcal* infection or from an individual at risk of having been exposed to a group B *streptococcus*. Further, the presence of an epsilon antigen can be part of a routine screen or panel for detecting group B *streptococcus* serotype III, RDP III-3 (e.g., a prenatal or neonatal screen).

In an alternate embodiment of the diagnostic method of the present invention, the presence of the epsilon antigen in a sample (e.g., samples provided supra) is detected via the presence of nucleic acid sequences encoding Srr-2 protein. Nucleic acid sequences encoding Srr-2 protein can be detected using any well-known method including, but not limited to, northern blot analysis, Southern blot analysis, reverse-transcriptase PCR, PCR, microarray and the like. Due to the ease of use, it is generally desirable to detect the nucleic acid sequences using a PCR-based approach. In general, this involves contacting the sample with two or more PCR primers which specifically hybridize with nucleic acid sequences encoding Srr-2 protein or which flank the coding region of Srr-2 protein, subjecting the sample to multiple steps of PCR amplification and detecting the presence or absence of the amplified sequence (e.g., using gel analysis, blotting methods, or fluorescently-labeled primers). Alternatively, an oligonucleotide, an aptamer, a cDNA, an antibody, or a fragment thereof, which interacts with at least a portion of the nucleic acid sequence encoding epsilon antigen is configured in an array on a chip or wafer and used for detecting nucleic acid sequences encoding epsilon. Briefly, these techniques involve methods for analyzing large numbers of genes rapidly and accurately. By tagging genes with oligonucleotides or using fixed probe arrays, one can employ chip technology to segregate target molecules as high density arrays and screen these molecules on the basis of hybridization (see, e.g., Pease, et al. (1994) *Proc. Natl. Acad. Sci. USA* 91(11): 5022-6; Fodor, et al. (1991) *Science* 251(4995):767-73).

Primers or oligonucleotides for use in this embodiment can be selected from any region of the locus encoding Srr-2 protein and generally specifically anneal and amplify at least a portion of nucleic acid sequences encoding Srr-2 protein and no other nucleic acid sequences encoding a closely related antigen. Suitable primers include those exemplified herein (e.g., SEQ ID NO:4 and SEQ ID NO:5) or can be selected by the skilled artisan from the sequence disclosed as SEQ ID NO:1. In general, the primers are 12 to 30 bp in length and generate a PCR amplicon of 50, 100, 200 400, 600, 1000 bp or more in length. In accordance with this method, a geometrically amplified product is obtained only when the first and second nucleotide sequences occur within the same nucleic acid molecule encoding the Srr-2 protein. The fundamentals of non-degenerate PCR are well-known to the skilled artisan, see, e.g. McPherson, et al., PCR, A Practical Approach, IRL Press, Oxford, Eng. (1991).

Typically, a positive or negative control can be included in such a diagnostic method to determine the accuracy of the method.

In accordance with the diagnostic method of the present invention, is a kit for identifying the presence of Srr-2 protein or epsilon antigen is also provided. A kit of the invention comprises a container containing a binding agent (e.g., an antibody) which specifically binds a group B *streptococcal* epsilon antigen (e.g., the carbohydrate and/or protein component). The kit can also contain other solutions necessary or convenient for carrying out the invention. The container can be made of glass, plastic or foil and can be a vial, bottle, pouch, tube, bag, etc. The kit may also contain written information, such as procedures for carrying out the present invention or analytical information, such as the amount of reagent contained in the first container means. The container can be in another container, e.g., a box or a bag, along with the written information.

As epsilon antigen is a surface antigen of group B *streptococcus* serotype III, RDP III-3, the present invention further relates to a vaccine containing an epsilon antigen or Srr-2 protein for preventing a group B *streptococcal* infection such as that of serotype III, RDP III-3. A vaccine can include an isolated epsilon antigen or Srr-2 protein, or an antigenic fragment thereof, and a pharmaceutically acceptable carrier. Active immunization can be induced by administering one or more antigenic and/or immunogenic epitopes of an epsilon antigen or Srr-2 protein as a component of a vaccine. Vaccination can be performed orally, nasally or parenterally in amounts sufficient to enable the recipient to generate protective antibodies against this biologically functional region, prophylactically or therapeutically. The host can be actively immunized with an antigenic/immunogenic epsilon antigen or Srr-2 protein in pure form, a fragment of the protein, or a modified form of the protein. One or more amino acids, not corresponding to the original protein sequence can be added to the amino or carboxyl terminus of the original peptide, or truncated form of peptide. Such extra amino acids are useful for coupling the protein to another peptide, to a large carrier protein, or to a support which can enhance the immunological response to the vaccine. Amino acids that are useful for these purposes include: tyrosine, lysine, glutamic acid, aspartic acid, cysteine and derivatives thereof. Alternative protein modification techniques can be used, e.g., $NH_2$-acetylation or COOH-terminal amidation, to provide additional means for coupling or fusing the protein/peptide to another protein or peptide molecule or to a support. In addition to a pharmaceutically acceptable carrier, the Srr-2 protein or epsilon antigen, or antigenic fragment thereof, can be co-administered with an adjuvant to enhance the immunological response to the vaccine.

The present invention further relates to a method for identifying an agent which blocks adhesion of a group B *streptococcus* serotype III, RDP III-3. In general, the method involves contacting a *streptococcus* cell expressing an epsilon antigen with a test agent and measuring the expression or activity of the epsilon antigen as compared to a control. In one embodiment of this method, the expression of an epsilon antigen is measured by determining the amount of mRNA encoding epsilon antigen/Srr-2 protein or the amount of epsilon antigen glycoprotein. Amounts of mRNA encoding epsilon antigen/Srr-2 protein can be detected using any well-known method (e.g., northern blot analysis, RT-PCR, and the like). Amounts of epsilon antigen glycoprotein can be determined by, for example, western blot analysis or reporter gene expression wherein the reporter is operably linked to the Srr-2 promoter thereby reflecting the level of expression of the epsilon antigen. Suitable reporters (e.g., luciferase or green fluorescent protein) and methods of using the same are well-known in the art. An exemplary control for use in the method of the invention includes a cell which has not been contacted with a test agent.

In another embodiment of this method of the invention, the activity of epsilon antigen can be determined by cell adhesion assays. In general, a cell adhesion assay involves contacting a *streptococcus* cell expressing an epsilon antigen with a test agent and measuring the adhesion of said *streptococcus* to a host cell (e.g., a mammalian tissue or cell culture or host animal) as compared to a same *streptococcal* cell which has not been contacted with the test agent. Such adhesion assays are well-known within the art (e.g., see Bensing and Sullam (2002) supra; Wu and Fives-Taylor (1999) supra; Wu et al. (1998) supra).

Further, the activity of a test agent can be determined in vivo by administering a test animal a test agent and determining whether said test agent provides protection or treatment against a GBS infection. To illustrate, a CD-1 mouse is administered a test agent (e.g., and anti-epsilon antigen antibody) and subsequently challenged with an amount of J48 *streptococcal* strain corresponding to the $LD_{90}$. The mice are than monitored for survival to evaluate the effectiveness of the antibody to block adhesion of *streptococcal* cells to the host.

Agents which modulate the expression or activity of an epsilon antigen can be identified by screening a library of test agents. Agents are obtained from a wide variety of sources including libraries of synthetic or natural compounds. A library can comprise either collections of pure agents or collections of agent mixtures. Examples of pure agents include, but are not limited to, antibodies (e.g., as disclosed herein), peptides, peptide aptamers, polypeptides, oligonucleotides, carbohydrates, fatty acids, steroids, purines, pyrimidines, lipids, synthetic or semi-synthetic chemicals, and purified natural products, derivatives, structural analogs or combinations thereof. Examples of agent mixtures include, but are not limited to, extracts of prokaryotic or eukaryotic cells and tissues, as well as fermentation broths and cell or tissue culture supernatants. In the case of agent mixtures, one may not only identify those crude mixtures that possess the desired activity, but also monitor purification of the active component from the mixture for characterization and development as a therapeutic drug. In particular, the mixture so identified can be sequentially fractionated by methods commonly known to those skilled in the art which may include, but are not limited to, precipitation, centrifugation, filtration, ultrafiltration, selective digestion, extraction, chromatography, electrophoresis or complex formation. Each resulting subfraction can be assayed for the desired activity using the original assay until a pure, biologically active agent is obtained.

Agents of interest in the present invention are those with functional groups necessary for structural interaction with proteins or carbohydrates, particularly hydrogen bonding, and typically include at least an amine, carbonyl, hydroxyl or carboxyl group, preferably at least two of the functional chemical groups. The agents often comprise cyclical carbon or heterocyclic structures and/or aromatic or polyaromatic structures substituted with one or more of the above functional groups.

An agent which blocks or inhibits the expression or activity of an epsilon antigen will be useful as a therapeutic or prophylactic agent for treating or preventing *streptococcal* infection via inhibiting adhesion of a *streptococcal* cell to a host cell. For example, an agent of the present invention would be useful in reducing the number of streptococci in a pregnant mother thereby reducing the incidence of neonatal sepsis.

Accordingly, the present invention further encompasses preventing or treating a *streptococcal* infection or disease in a subject by administering to a subject having, or at risk of having, a *streptococcal* infection or disease an effective amount of an agent that inhibits the expression or activity of an epsilon antigen.

As used herein, an effective amount of an agent which inhibits the expression or activity of an epsilon antigen or, as disclosed herein, is targeted to a bacterial cell via a binding agent, is an amount which prevents, eliminates or alleviates at least one sign or symptom of a *streptococcal* infection or disease. Signs or symptoms associated with a *streptococcal* infection or disease include, but are not limited to, bacterial colonization, sepsis, meningitis, or pneumonia. The amount of the agent required to achieve the desired outcome of preventing, eliminating or alleviating a sign or symptom of a *streptococcal* infection or disease will be dependent on the pharmaceutical composition of the agent, the patient and the condition of the patient, and the mode of administration.

A pharmaceutical composition is one that contains the agent and a pharmaceutically acceptable carrier. A pharmaceutically acceptable carrier is a material useful for the purpose of administering the medicament, which is preferably sterile and non-toxic, and can be solid, liquid, or gaseous materials, which is otherwise inert and medically acceptable, and is compatible with the active ingredients. A generally recognized compendium of methods and ingredients of pharmaceutical compositions is Remington: The Science and Practice of Pharmacy, Alfonso R. Gennaro, editor, 20th ed. Lippincott Williams & Wilkins: Philadelphia, Pa., 2000.

A pharmaceutical composition can contain other active ingredients such as preservatives. A pharmaceutical composition can take the form of a solution, emulsion, suspension, ointment, cream, granule, powder, drops, spray, tablet, capsule, sachet, lozenge, ampoule, pessary, or suppository. It can be administered by continuous or intermittent infusion, parenterally, intramuscularly, subcutaneously, intravenously, intra-arterially, intrathecally, intraarticularly, transdermally, orally, bucally, intranasally, as a suppository or pessary, topically, as an aerosol, spray, or drops, depending upon whether the preparation is used to treat an internal or external condition or disease. Such administration can be accompanied by pharmacologic studies to determine the optimal dose and schedule and would be within the skill of the ordinary practitioner.

While the present invention relates to the identification of a novel group B *streptococcal* surface antigen designated epsilon antigen, it is further contemplated that loci flanking the gene encoding epsilon antigen (i.e., the Srr-2 locus) would also be useful as potential targets for diagnostics, vaccines and the like disclosed herein. For example, the glycosyltransferases and accessory secretory proteins (Asp1 and Asp2), are also unique to RDP III-3 strains having the accessory secAY2-A2 locus.

The invention is described in greater detail by the following non-limiting examples.

EXAMPLE 1

Bacterial Strains and Growth Conditions

GBS strains used herein are listed in Table 3. Strains DL797, DL769, DL771, DL686, DL775, DL1104 and DL700 were clinical isolates from the University of South Florida (Tampa, Fla.). GBS strains representing RDP III types 1-4 were isolated from vaginal swabs, blood, or cerebrospinal fluid using standard methods (Takahashi, et al. (1998) supra). Strain NEM316 (serotype III, RDP III-1), an isolate from an infected infant (Glaser, et al. (2002) supra), was obtained from American Type Culture Collection (ATCC12403; Manassas, Va.). All streptococci were grown to late exponential phase in Todd-Hewitt broth (THB; Becton Dickinson, Cockeysville, Md.) at 37° C. without shaking. *E. coli* strain TOP10 was grown in Luria-Bertani (LB) broth at 37° C. with shaking.

TABLE 3

| Strain | Serotype | Surface Antigen[†] | RDP Type |
|---|---|---|---|
| A909[a] | Ic | alpha/beta/gamma/delta | ND |
| ss618[b] | Ib | alpha/beta/gamma | ND |
| 9B200[b] | II | none | ND |
| J48[b] | III | delta/epsilon | III-3 |
| J52[b] | III | delta/epsilon | III-3 |
| PEH[b] | III | delta/epsilon | III-3 |
| COH1[c] | III | delta/epsilon | III-3 |
| COH1-13[c] | III | delta/epsilon | III-3 |
| 874391 | III | delta/epsilon | III-3 |
| DL797 | III | delta/epsilon | ND |
| DL769 | III | delta/epsilon | ND |
| DL771 | III | delta/epsilon | ND |
| DL686[b] | III | none | ND |
| DL775 | III | none | ND |
| DL1104 | III | none | ND |
| DL700[b] | III | none | III-2 |
| NEM316[d] | III | none | III-1 |
| 865043[e] | III | none | III-2 |

[†]Surface antigens associated with C-protein
ND, not determined.
[a]Obtained from the Centers for Disease Control and Prevention (Atlanta, GA).
[b]Clinical isolates from Shands Hospital (University of Florida, Gainesville, FL).
[c]Wilkinson and Eagon (1971) supra.
[d]Glaser, et al. (2002) supra.
[e]Takahashi, et al. (1998) supra.

EXAMPLE 2

Generation of Polyclonal Anti-Epsilon Antigen Antiserum

Polyclonal rabbit antiserum was produced by immunization of a New Zealand white rabbit with formalin-killed cells, followed by adsorption with appropriate GBS strains. Cells from a 200 mL stationary phase culture of GBS strain J48 were killed by treatment with 10 mL of a 4% formalin, 0.85% saline solution at 4° C. overnight. The density of the immunogen was adjusted to an $OD_{660}$ of 0.4. A rabbit was injected intravenously with 0.5 mL of the bacterial suspension 3 times per week for 1 week and then with 1 mL of the bacterial suspension 3 times per week for 3 weeks. The rabbit was rested for 3 weeks and then injected with 1 mL of the bacterial suspension 3 times per week for 2 weeks. The rabbit was exsanguinated by cardiac puncture under anesthesia. Serum was stored at −20° C.

EXAMPLE 3

Two-Stage Radioimmunoassay (RIA)

A two-stage radioimmunoassay was performed according to standard methods (Brady, et al. (1988) supra). Briefly, bacteria from 10 mL, 16 hour cultures of the indicated strains of GBS were harvested by centrifugation for 8 minutes at 1,000×g and suspended in 2 mL phosphate-buffered saline (PBS) to a final concentration of ~1×10$^{10}$ bacteria/mL. One hundred microliters of each bacterial suspension were mixed with an equal volume of unadsorbed or adsorbed anti-J48 antiserum (1:1000 dilution) and incubated for 1 hour at 37° C. Bacteria were pelleted by centrifugation and washed twice with 2 mL of PBS to remove unbound antibodies. Following the second wash, cells were suspended in the residual buffer (~100 μL) and incubated with 100 μL of $^{125}$I-labeled protein A (Amersham Biosciences-GE Healthcare, Piscataway, N.J.) containing ~30,000 cpm for 1 hour at 37° C. Cells were washed twice to remove the unbound tracer, and radioactivity associated with the bacterial pellets was determined using a Gamma 5500 (Beckman Coulter, Fullerton, Calif.) gamma counter. All assays were performed in duplicate with less than 5% variation observed between replicate samples. Reactivity of each strain with normal rabbit antiserum was tested as a negative control.

EXAMPLE 4

Epsilon Antigen Expression by RDP III Types 1-4

GBS strains representative of RDP types 1-4 were assayed for epsilon antigen expression by ELISA. COSTAR® High Binding plates (COSTAR®, Corning, N.Y.) were coated overnight at 4° C. in a moist chamber with 100 μL of 0.1 M carbonate-bicarbonate buffer (pH 9.6) containing 0.02% sodium azide and approximately 10$^7$ colony forming units of *streptococcal* cells of the indicated strain. Prior to antibody binding, plates were blocked with PBS plus 0.03% TWEEN™-20 (PBS-T). Test wells were incubated with 100 μL of polyclonal anti-epsilon antigen antibody (1:100 dilution in PBS) for 2 hours at 37° C. After washing three times with 300 μL PBS-T, 100 μL of affinity-purified HRP-labeled goat-anti-rabbit secondary antibody (1:1000 dilution in PBS, MP Biomedicals, Inc, Aurora, Ohio) was added to the wells for 2 hours at 37° C. Plates were washed, and developed with 0.4 mg/mL o-phenylenediamine (OPD) in 0.1 M citric acid/0.2 M sodium phosphate buffer, pH 4.5, in the presence of 0.03% hydrogen peroxide. Absorbance at $OD_{450}$ of test wells was determined using a Model 550 microplate reader (BIO-RAD®, Hercules, Calif.). Control wells included secondary antibody alone to determine background $OD_{450}$ values. All assays were performed in duplicate with less than 5% variation observed between replicate samples.

EXAMPLE 5

Evaluation of Lethal Dose

A neonatal mouse model of infection was used to compare the lethal dose 90% ($LD_{90}$) values of serotype III/delta/epsilon-positive and serotype III/delta/epsilon-negative strains. Eight to fourteen offspring from one dam were inoculated intraperitoneally with a given challenge dose (from 10$^2$-10$^8$ colony-forming units) diluted in 100 μL of THB 24-48 hours after birth. Deaths were recorded for 72 hours post-inoculation. $LD_{90}$ values were determined using standard methods (Reed and Muench (1938) *Am. J. Hyg.* 27:493). The $LD_{90}$ values were grouped according to δ/ε expression and compared using a two-sample t-test of log transformed data.

EXAMPLE 6

Extraction of Epsilon Antigen and Anion-Exchange Chromatography

Extracts of GBS were prepared by sonicating 4 grams (wet weight) of GBS strain J48 in 4 mL of 20 mM Tris-HCl pH 8.0 with 4 grams of P-800 Potter's glass beads three times for 30 seconds each on ice with a Sonic 300 Dismembrator (ARTEK Systems Corporation, Farmingdale, N.Y.). The glass beads and bacterial debris were removed from the sonicated mixture by centrifugation at 10,000×g for 5 minutes. The resulting extract was centrifuged in a Beckman L7-55 Ultracentrifuge>100,000×g for 2 hours to remove wall-membrane complexes. The supernatant was collected and filtered through 0.2 μm ACRODISCS® (Gelman Sciences, Ann Arbor, Mich.), diluted 1:3 in 20 mM Tris-HCl pH 8.0, and loaded onto an UNO-Q1 anion-exchange column (BIO-RAD®, Hercules, Calif.). Unbound material was removed from the column by washing with 2.5 column volumes of 20 mM Tris-HCl pH 8.0. Bound molecules were eluted from the column using a stepwise gradient of 0-1 M NaCl of 0.05 M NaCl increments in 20 mM Tris-HCl pH 8.0.

EXAMPLE 7

Competition ELISA and Western Immunoblot

Approximately 10$^7$ J48 (serotype III/δε) whole cells were used to coat 96-well microtiter plates (COSTAR®, Corning N.Y.). After blocking with PBS-Tw test wells were incubated with 100 μL of individual column fractions from anion-exchange chromatography and 100 μL of anti-epsilon antigen polyclonal rabbit antibody (1:100 dilution in PBS) for 2 hours at 37° C. After washing, wells were incubated with horseradish peroxidase (HRP)-labeled goat-anti-rabbit conjugate at a 1:1000 dilution (MP Biomedicals, Inc, Aurora, Ohio) for 2 hours at 37° C. Plates were then washed and developed with OPD. Percent inhibition was determined by comparing $OD_{450}$ values of test wells with $OD_{450}$ values of wells containing 100 μL of buffer only instead of a column fraction (0% inhibition). Results are given as % inhibition. Proteins contained in anion-exchange column fraction #14 from both J48

(serotype III/δε), which contained epsilon antigen as determined by competition ELISA, and DL700 (serotype III) were separated on 7.5% SDS-polyacrylamide gels and electroblotted onto a PROTRAN® nitrocellulose membrane (Schleicher & Schuell, Keene, N.H.) and blocked with PBS-T. The membrane was incubated with monospecific anti-epsilon antigen polyclonal rabbit antibody (1:100) overnight at room temperature. After washing, the blot was incubated with HRP-labeled goat-anti-rabbit conjugate at a 1:1000 dilution (MP Biomedicals) for 2 hours at room temperature, washed, and developed with ECL™ detection reagents (Amersham Life Sciences, San Francisco, Calif.).

EXAMPLE 8

Proteinase K or Sodium Metaperiodate Treatment

Approximately $10^7$ cell of J48 (serotype III/delta/epsilon) were used to coat 96-well microtiter plates (COSTAR®, Corning, N.Y.). Test wells were incubated with 100 µL of either PBS or PBS containing 0.05% proteinase K (Sigma Chemical Co., St. Louis, Mo.) for 2 hours at room temperature, or 0.05 M sodium acetate buffer pH 5.5 or acetate buffer containing 0.05 M sodium metaperiodate (Sigma Chemical Co.) for 16 hours at room temperature, after which the proteinase K or sodium metaperiodate was removed from test wells with multiple washes with PBS-T. Wells were incubated with 100 µL of anti-epsilon polyclonal rabbit antibody (1:100 dilution in PBS) for 2 hours at 37° C. After washing, wells were incubated with HRP-labeled goat-anti-rabbit at a 1:1000 dilution (ICN Biomedicals) for 2 hours at 37° C. Plates were washed and developed with OPD.

EXAMPLE 9

Elution of Epsilon Antigen-Containing Material

One mL (1.6 mg/mL) of sonic extracts of strains J48 and DL700 were separated on multiple 1.5 mm-thick 7.5% preparatory SDS-polyacrylamide gels (8.6×6.8 cm). A 2 mm gel-slice (from the 250-kDa protein standard and above) containing the epsilon antigen in the J48 (serotype III/delta/epsilon) sample or the corresponding material from DL700 (serotype III) was excised from each gel. The gel slices were each finely minced with a razor blade and material was eluted from the minced gel slices with 500 μL of 50 mM ammonium bicarbonate pH 7.4, 1% SDS added to each tube. Tubes were allowed to rock for 2 hours at 37° C. The supernatant from each tube was removed and pooled according to strain. This extracted material was analyzed by western immunoblot. Multiple samples of the eluted material from both J48 (serotype III/delta/epsilon) and DL700 (serotype III) and the sonic extract starting material were separated on 7.5% SDS-polyacrylamide gels, electroblotted onto nitrocellulose membranes (PROTRAN®, Schleicher & Schuell), and blocked with PBS-T. The membranes were incubated with anti-epsilon antigen, anti-delta antigen, and anti-serotype III polyclonal rabbit antibody overnight at room temperature. After washing, the blots were incubated with HRP-labeled goat-anti-rabbit conjugate at a 1:1000 dilution (MP Biomedicals, Inc) for 2 hours at room temperature, washed, and developed with ECL™ detection reagents (Amersham Life Sciences). The eluted material was assayed for the presence of group B carbohydrate by latex agglutination (PHADABACT®, Boule Diagnostics, Huddinge, Sweden). Amino acid and carbohydrate content of the eluted samples was also conducted.

EXAMPLE 10

PCR Amplification

Pairs of forward and reverse primers (KS51 and KS53) were used to amplify open reading frames from strain DL700 (III), a RDP III-1 strain, and J48 (serotype III/delta/epsilon), a RDP III-3 strain (Table 4). PCR primers were designed based on the srr gene sequence from the NEM316 genome (Glaser, et al. (2002) supra) or contained within the DY-3 clone unique to RDP III-3 GBS (Bohnsack et al. (2002) supra). DNA was first denatured at 94° C. for 1 minute. Subsequently, thirty amplification cycles were performed as follows: 1 minute of denaturation at 94° C., 1 minute of annealing at 55° C., and 2 minutes of extension at 72° C., followed by one cycle of 5 minutes at 72° C. PCR products was analyzed by gel electrophoresis in 0.7% agarose.

TABLE 4

| Primer Name (F/R) | Sequence 5'-3' | Gene Amplified | SEQ ID NO: |
|---|---|---|---|
| KS13 (F) | ATGTCCCAAAAGACTTTTGGC | gbs1529 (srr-1)[a] | 6 |
| KS14 (R) | CGTCCCAAAAGGGTTGCACCAGTCA | gbs1529 (srr-1)[a] | 7 |
| KS31 (F) | ATGTCACGCAGTCAAAAAGTTA | gbs1514 (mutT)[a] | 8 |
| KS32 (R) | ACCATCTTCAAGTCGCTTACT | gbs1514 (mutT)[a] | 9 |
| KS39 (F) | TGATAGTTACACTCAATCAAGTT | gbs1516[a] | 10 |
| KS40 (R) | CTGAGTAGAGCTTGAAACATG | gbs1516[a] | 11 |
| KS41 (F) | AACCATGGAATTGGTTGGGC | gbs1517[a] | 12 |
| KS42 (R) | AACCATGGAATTGGTTGGGC | gbs1517[a] | 13 |
| KS33 (F) | ATGACAGCCTTTAATAGTTTATTT | gbs1518 (secA2)[a] | 14 |
| KS34 (R) | AAGATCTCCATTCTCATTGAAG | gbs1518 | 15 |
| KS35 (F) | CCTGGTGTCTTGATTTCTGCT | (secA2)[a]gbs1522 | 16 |
| KS36 (R) | TTCTCCTCATTTTCAAATACAGA | (secY2)[a]gbs1522 | 17 |

TABLE 4-continued

| Primer Name (F/R) | Sequence 5'-3' | Gene Amplified | SEQ ID NO: |
|---|---|---|---|
| KS24 (F) | AGCTATCGCGTTAGCGGCA | (secY2)[a] | 18 |
| KS30 (R) | GCCTTGACCATGATAAGTTGT | gbs1526[a] | 19 |
| KS26 (F) | GGTGCAGATTTCCAATATCGT | gbs1526[a] | 20 |
| KS27 (R) | TCATCTAAGAGGACCTACTTC | gbs1527[a] | 21 |
| KS28 (F) | TTGCGAGTACATATTACAAGTAT | gbs1527[a] | 22 |
| KS29 (R) | ATCTATAAAGCATATGCACAGC | gbs1528[a] | 23 |
| KS22 (F) | GATACCCCTCACTATCCTT | gbs1528[a] | 24 |
| KS23 (R) | GATATTACTGATTTGAGAGGGT | gbs1530 (rofA)[a] | 25 |
| KS20 (F) | ATAGATAGAAAAGATACTAACCG | gbs1530 (rofA)[a] | 26 |
| KS21 (R) | TGCAGCTAGCTCAAAGTCCAATAAT | gbs1531 (uvrB)[a] | 27 |
| KS51 (F) | TCACGCAAAGTTCGAGTTAAAA | gbs1531 (uvrB)[a] | 4 |
| KS53 (R) | CGCAGATTTAGTAGCTCCTAA | srr-2[b] | 5 |
|  |  | srr-2[b] |  |

F = Forward; R = Reverse
[a] Reference source is NEM316 which refers to the published genome sequence by Glaser, et al. (2002) supra.
[b] Reference source is DY-3 which refers to the RDP III-3 genomic clone described by Bohnsack, et al. (2002) supra.

EXAMPLE 11

Cloning RDP Type III-3-Specific Genomic DNA

A 874391 genomic phage library was screened with an RDP type III-3-specific probe DY-3 and an 8816 bp genomic DNA fragment hybridizing with this probe was purified and subcloned using standard methods (Adderson, et al. (2003) *Infect. Immun.* 71(12):6857-63). The nucleotide sequence of this clone was determined by transposon-mediated shotgun sequencing (Ribot, et al. (1998) *Biotechniques* 24(1):16-7, 20, 22). Sequences were processed through the Phred program (Ewing, et al. (1998) *Genome Res.* 8(3):175-85) to generate base calls and base quality values and assembled using the Phrap (version 0.990329) program.

The ~3.6 kb nucleic acid sequence encoding to open reading frame of Srr-2 from DY-3 is presented as SEQ ID NO:1. The Srr-2 protein sequence encoded by SEQ ID NO:1 is provided as SEQ ID NO:2. A ~24 kb SecY2-A2 locus from J48 was also identified and sequenced (SEQ ID NO:28). This locus contained the open reading frames listed in Table 5. It is contemplated that unique nucleic acid sequences within these open reading frames can also be used for diagnosing a GBS RDP III-3 infection. Moreover, because the order of these open reading frames is unique to RDP III-3, primers can be generated to any two of the open reading frames to amplify a product unique to GBS RPD III-3.

TABLE 5

| Nucleotide position* | Length (nt) | Gene Name | Protein Function |
|---|---|---|---|
| 285-1442 | 1158 | Hyp | (SAM)-dependent methyltransferase |
| 1442-2119 | 678 | AroD | 3-dehydroquinate dehydratase |

TABLE 5-continued

| Nucleotide position* | Length (nt) | Gene Name | Protein Function |
|---|---|---|---|
| 2213-3280 | 1068 | AroB | 3-dehydroquinate synthase |
| 3281-4447 | 1167 | AroC | chorismate synthase |
| 4531-4866 | 336 | Hyp | unknown |
| 5606-8953 | 3348 | srr-2 | serine-rich repeat-2 protein |
| 9063-10316 | 1254 | secY2 | SecY2 |
| 10326-11903 | 1578 | asp1 | Accessory Protein 1 |
| 11905-13494 | 1590 | asp2 | Accessory Protein 2 |
| 13466-14032 | 567 | asp3 | Accessory Protein 3 |
| 14029-16425 | 2397 | secA2 | SecA2 |
| 16441-17961 | 1521 | gtfA | glycosyltransferase A |
| 17945-19273 | 1329 | gtfB | glycosyltransferase B |
| 19553-20482 | 930 | nss | nucleotide sugar synthetase |
| 20490-22202 | 1713 | gly | glycosyltransferase |
| 22326-23675 | 1350 | gor | glutathione reductase |

*Nucleotide position referring to that of SEQ ID NO: 28.

EXAMPLE 12

Cloning, Expression, and Western Immunoblot of Recombinant Srr-2 from J48

The sequenced DNA from the DY-3 clone contained on open reading frame of 3.6 kb predicted to encode a protein with a di-serine (XS) motif for approximately two-thirds of the protein, designated srr-2 for serine-rich repeat 2 protein. The srr-2 gene from GBS strain J48 (serotype III/delta/epsilon) was amplified by PCR using primers KS51 and KS53 according to methods disclosed herein. The amplified product was ligated to pBAD-TOPO® (INVITROGEN™, Carlsbad, Calif.) expression vector and used to transform *E. coli* strain TOP10 according to the manufacturer's protocol. The resulting plasmid was designated pKS60. Correct orientation and reading frame with the C-terminal V5 epitope was confirmed by sequence analysis, using the universal primers supplied with the pBAD-TOPO® kit. Ten milliliters of mid-log phase E. coli cells ($OD_{600}$=0.5) harboring pKS60 was induced to express recombinant Srr with 10-fold decreases of L-arabinose (from 2-0.0002%). Cells were grown for 4 hours after induction. Cells were then harvested by centrifugation and resuspended in 1 mL of 1×SDS-sample buffer. The cells were boiled for 5 minutes and pelleted. Fifty microliters of the supernatant were separated on 7.5% SDS-polyacrylamide gels and electroblotted onto PROTRAN® nitrocellulose membranes (Schleicher & Schuell) and blocked with PBS-T. One membrane was incubated with anti-V5 monoclonal antibody (INVITROGEN™, Carlsbad, Calif.) at a 1:5000 dilution overnight at room temperature. After washing, the blot was incubated with HRP-labeled goat-anti-mouse (H+L chain) at a 1:1000 dilution (MP Biomedicals, Inc, Aurora, Ohio) for 2 hours at room temperature, washed, and developed with 8 mL of 4-chloro-1-naphthol solution which consisted of 7 mL PBS, 1 mL 4-chloro-1-napthol (3 mg/mL in methanol; Sigma Chemical Company), and 8 µL of 30% hydrogen peroxide (Fisher Scientific, Pittsburgh, Pa.). The other membrane was incubated with anti-epsilon polyclonal rabbit antibody overnight at room temperature. After washing, the blot was incubated with HRP-labeled goat-anti-rabbit at a 1:1000 dilution (MP Biomedicals, Inc, Aurora, Ohio) for 2 hours at room temperature, washed, and developed with ECL™ detection reagents (Amersham Life Sciences).

EXAMPLE 13

DNA Hybridization

DNA hybridization was performed by the method of Southern (Sambrook et al. (1989) Molecular Cloning: A Laboratory Manual, 2nd ed., Cold Spring Harbor, N.Y., Cold Spring Harbor Laboratory Press). Chromosomal DNA from all GBS strains was isolated according to standard methods (Nagano et al. (1991) J. Med. Microbiol. 35(5):297-303) and further purified on CsCl gradients. Two micrograms of genomic DNA from each of the GBS strains tested was digested with EcoRV (PROMEGA®, Madison, Wis.) for 16 hours at 37° C. overnight. The digested DNA was separated by electrophoresis through 0.7% agarose gels and transferred to nylon membranes (Boehringer Mannheim, Indianapolis, Ind.) by a capillary blot procedure according to the manufacturer's instructions. One membrane was probed with the DL700 srr-1 ORF amplified with primers KS13 and KS14, and the other membrane was probed with the J48 srr-2 ORF amplified with primers KS51 and KS53, both labeled during PCR amplification with Digoxigenin-11-dUTP (DIG-dUTP, Boehringer Mannheim) at 42° C. overnight. The blots were developed according to the manufacturer's instructions.

What is claimed is:

1. An isolated serine-rich repeat protein-2 (Srr-2) or ϵ protein, wherein said protein comprises SEQ ID NO:2 or a fragment comprising at least 10 amino acid residues of SEQ ID NO:2.

2. A composition comprising an isolated protein of claim 1 and a pharmaceutically acceptable carrier.

* * * * *

SEQUENCE LISTING

<160> NUMBER OF SEQ ID NOS: 28

<210> SEQ ID NO 1
<211> LENGTH: 3615
<212> TYPE: DNA
<213> ORGANISM: Streptococcus agalactiae

<400> SEQUENCE: 1

```
atgttaaaaa agcagtttgg aaactttggt gaaaaatcac gcaaagttcg agttaaaatg      60
aggaaatcag gtaagcactg ggtcaaaagt gttatgacac aaattggcta tgttatcctt     120
tcgaggttta gcggtaaaga gaaaagctct aaggttcaaa ctactagtga agatttaagc     180
agaactaaaa cgtctgctag catcctaaca gcagtcgcag ctcttggagc tgtagttgga     240
gggacgacag acacaacttc tgtctcagct gaagaaacac tactgcaac agaacttaca     300 ggaaatgaaa aaacattagc tactgctgaa actgtagtgg ttgcgccaga agtaaaaact     360
gtaaactcag attcttcatc acattcaaca agtgaatcac aatcaatgtc aactagtacc     420
ttgcaatcta ccagcgcctc attatctgcc agtgaatcac taatggattc tacctctgct     480
tctttatctg agtctagctc gttatcagaa tatagttctt tatctctatc tagtagtgag     540
agtgtctcag catcagaatc agttcaatca tcagaagcgg caacgaccgc tagagttcaa     600
ccgagagcga tgagagttgt atctagtgct tcagatatgg aaactttacc agcagcatta     660
atctctggtg aaggagatgt aacaactgtt caaggacaag atgtaacaga taagttacaa     720
aatttagata taaagctctc tggaggagtg caagcaaaag caggtgttat aaatatggat     780
aagtcagaaa gtatgcacat gtctttaaaa ttcactattg attctgtgaa tagaggtgat     840
acttttgaaa ttaagttatc agataatatc gatacaaatg gagcttctaa ctattctatt     900
gtagaaccta taaaatcacc tacgggtgag gtctatgcga ctggaattta tgattctcaa     960
```

```
aaaaaatcta tagtctatag ttttacagat tttgcggctt caaaaaataa tattaatgga   1020
atattagata ttccattatg gccagatgat acgacagttc aaaacacaaa agaagatgtt   1080
cttttttcgg taaaaataaa ggatcaagag gctacaatta aagaaacagt gaaatatgat   1140
ccaccggtaa gaattgattt tgcaggggga gtaagtgtag attctcgaat aaccaacatt   1200
gatgatgtgg gaaaaagat gacttatata agtcaaatta atgtagatgg aaaatcactc    1260
tataattaca acgggttata tactaggata tataattata gcaaagagag tacagcagat   1320
ttaaagaatt caacgataaa aatctataaa accacctcgg ataatattgt agagagtatg   1380
gtacaggatt attcaagcat ggaggatgta actagtaagt ttgcaaatag ttacccagaa   1440
aaagggtggt atgatattta ttgggggcag tttattgcat caaatgaaac gtatgtaatt   1500
gttgtagaaa caccatttac taatgcagta actttgaata ctactttatc agattataat   1560
gagaacaatg gtgtagaaca taatcatact tactcatctg aatcgggata ttcagatgta   1620
aatgctcaag aaagaaaaat tttatccgaa ttagtaagta gctcagaatc agtatcaagt   1680
tcagaatcgg tatctaattc cgaatctatt tcaacttctg aatcggtatc taactccgag   1740
tctatttcaa gttccgaatc ggtatcaagc tcagaatcta tttcaacttc tgaatcggta   1800
tcaacttcag agtctatttc aagctccgag tcagtatcaa gttcagaatc ggtatcaagc   1860
tcagaatcta tttcaagttc cgaatcggta tctaactccg agtctatttc aagctccgaa   1920
tcggtatcta actccgaatc catttcaagt tctgaatcgg tatcaagctc agaatctatt   1980
tcgaattcag agtctatttc aagctccgag tcagtatcaa cttcagagtc tatttcaagc   2040
tccgaatcgg tatctaactc cgaatccatt tcaagttctg aatcggtatc aagctcagaa   2100
tctatttcga attcagagtc tatttcaagc tccgagtcag tatcaacttc agagtctatt   2160
tcaaactccg agtcggtatc tagctccgag tcagtatcaa cttcagagtc tatttcaagt   2220
tccgaatcgg tatctaactc cgaatccatt tcaacttccg agtcagtatc tacctcggaa   2280
tctatttcaa gttctgaatc ggtatcaagc tcagaatcta tttcaagttc cgaatcggta   2340
tcaaactccg agtctatttc aaactccgag tcggtatcta gctccgagtc agtatcaaat   2400
tcagagtcta tttcaagttc cgaatcggta tctaactccg aatccatttc aacttccgag   2460
tcagtatcta cctcggaatc tatttcaagt tctgaatcgg tatcaaattc agagtctatt   2520
tcaagttccg aatcggtatc taactccgag tctatttcaa gttcagaatc ggtatcaaat   2580
tcagagtcta tttcaagttc cgaatcggta tcaaattcag agtctatttc aagttcagag   2640
tcagtatcaa gttcagagtc agtatcaagc tcggaatcta tttcaacttc cgaatcggta   2700
tctaactccg agtctatttc aagttccgaa tcggtatcta attctgaatc tatttcaagt   2760
tccgaatcgg tatcaaattc agagtctatt tcaagttccg aatcggtatc aaactccgag   2820
tctatttcaa gttccgagtc agtatcaagc tcagaatcta tttcaagttc cgaatcggta   2880
tcaagctccg agtcagtatc aaattcagag tctatttcaa gttccgaatc ggtatctaac   2940
tccgagtcta tttcaagttc agaatcggta tcaacttcag agtctatttc aagttccgaa   3000
tcggtatcaa attcagagtc tatttcaagt tcagagtcag tatcaagttc agagtcagta   3060
tcaagctcgg aatctatttc aacttcagaa tcggtatcta actccgagtg tatttcaagt   3120
tccaaatcgg tatctaattc tgaatctatt tcaagttccg aatcggtatc aaattcagag   3180
tctatttcaa gttccgaatc ggtatcaaac tccgagtcta tttcaagttc cgagtcagta   3240
tcaagctcag aatctatttc aagttcagaa tcggtatcaa actccgagtc tattttaagt   3300
tccgaatcag tatcaagctc agaatctatt tcaagttcag aatctatttc aagttccgag   3360
```

-continued

```
tcagtatcaa tgagtactac agagtctcta agtgaatcag aagtatcagg ggattctgaa      3420
attagctcaa gtacagaatc atcaagtcaa tctgaatcga tgaatcatac tgaaattaaa      3480
tccgattccg aatctcaaca cgaagttaag catcaagtat taccagaaac aggtgataac      3540
tcggcttcag cattaggtct gttaggtgca ggattgttgt taggagctac taaatctcgc      3600
aagaagaaaa aagat                                                       3615
```

<210> SEQ ID NO 2
<211> LENGTH: 1205
<212> TYPE: PRT
<213> ORGANISM: Streptococcus agalactiae

<400> SEQUENCE: 2

```
Met Leu Lys Lys Gln Phe Gly Asn Phe Gly Glu Lys Ser Arg Lys Val
1               5                   10                  15

Arg Val Lys Met Arg Lys Ser Gly Lys His Trp Val Lys Ser Val Met
            20                  25                  30

Thr Gln Ile Gly Tyr Val Ile Leu Ser Arg Phe Ser Gly Lys Glu Lys
        35                  40                  45

Ser Ser Lys Val Gln Thr Thr Ser Glu Asp Leu Ser Arg Thr Lys Thr
    50                  55                  60

Ser Ala Ser Ile Leu Thr Ala Val Ala Ala Leu Gly Ala Val Val Gly
65                  70                  75                  80

Gly Thr Thr Asp Thr Thr Ser Val Ser Ala Glu Glu Thr Pro Thr Ala
                85                  90                  95

Thr Glu Leu Thr Gly Asn Glu Lys Thr Leu Ala Thr Ala Glu Thr Val
            100                 105                 110

Val Val Ala Pro Glu Val Lys Thr Val Asn Ser Asp Ser Ser Ser His
        115                 120                 125

Ser Thr Ser Glu Ser Gln Ser Met Ser Thr Ser Thr Leu Gln Ser Thr
    130                 135                 140

Ser Ala Ser Leu Ser Ala Ser Glu Ser Leu Met Asp Ser Thr Ser Ala
145                 150                 155                 160

Ser Leu Ser Glu Ser Ser Ser Leu Ser Glu Tyr Ser Ser Leu Ser Leu
                165                 170                 175

Ser Ser Ser Glu Ser Val Ser Ala Ser Glu Ser Val Gln Ser Ser Glu
            180                 185                 190

Ala Ala Thr Thr Ala Arg Val Gln Pro Arg Ala Met Arg Val Val Ser
        195                 200                 205

Ser Ala Ser Asp Met Glu Thr Leu Pro Ala Ala Leu Ile Ser Gly Glu
    210                 215                 220

Gly Asp Val Thr Thr Val Gln Gly Gln Asp Val Thr Asp Lys Leu Gln
225                 230                 235                 240

Asn Leu Asp Ile Lys Leu Ser Gly Gly Val Gln Ala Lys Ala Gly Val
                245                 250                 255

Ile Asn Met Asp Lys Ser Glu Ser Met His Met Ser Leu Lys Phe Thr
            260                 265                 270

Ile Asp Ser Val Asn Arg Gly Asp Thr Phe Glu Ile Lys Leu Ser Asp
        275                 280                 285

Asn Ile Asp Thr Asn Gly Ala Ser Asn Tyr Ser Ile Val Glu Pro Ile
    290                 295                 300

Lys Ser Pro Thr Gly Glu Val Tyr Ala Thr Gly Ile Tyr Asp Ser Gln
305                 310                 315                 320
```

-continued

```
Lys Lys Ser Ile Val Tyr Ser Phe Thr Asp Phe Ala Ala Ser Lys Asn
            325                 330                 335

Asn Ile Asn Gly Ile Leu Asp Ile Pro Leu Trp Pro Asp Thr Thr
        340                 345                 350

Val Gln Asn Thr Lys Glu Asp Val Leu Phe Ser Val Lys Ile Lys Asp
        355                 360                 365

Gln Glu Ala Thr Ile Lys Glu Thr Val Lys Tyr Asp Pro Pro Val Arg
370                 375                 380

Ile Asp Phe Ala Gly Gly Val Ser Val Asp Ser Arg Ile Thr Asn Ile
385                 390                 395                 400

Asp Asp Val Gly Lys Lys Met Thr Tyr Ile Ser Gln Ile Asn Val Asp
            405                 410                 415

Gly Lys Ser Leu Tyr Asn Tyr Asn Gly Leu Tyr Thr Arg Ile Tyr Asn
            420                 425                 430

Tyr Ser Lys Glu Ser Thr Ala Asp Leu Lys Asn Ser Thr Ile Lys Ile
            435                 440                 445

Tyr Lys Thr Thr Ser Asp Asn Ile Val Glu Ser Met Val Gln Asp Tyr
    450                 455                 460

Ser Ser Met Glu Asp Val Thr Ser Lys Phe Ala Asn Ser Tyr Pro Glu
465                 470                 475                 480

Lys Gly Trp Tyr Asp Ile Tyr Trp Gly Gln Phe Ile Ala Ser Asn Glu
                485                 490                 495

Thr Tyr Val Ile Val Val Glu Thr Pro Phe Thr Asn Ala Val Thr Leu
            500                 505                 510

Asn Thr Thr Leu Ser Asp Tyr Asn Glu Asn Asn Gly Val Glu His Asn
        515                 520                 525

His Thr Tyr Ser Ser Glu Ser Gly Tyr Ser Asp Val Asn Ala Gln Glu
    530                 535                 540

Arg Lys Ile Leu Ser Glu Leu Val Ser Ser Glu Ser Val Ser Ser
545                 550                 555                 560

Ser Glu Ser Val Ser Asn Ser Glu Ser Ile Ser Thr Ser Glu Ser Val
                565                 570                 575

Ser Asn Ser Glu Ser Ile Ser Ser Glu Ser Val Ser Ser Glu
            580                 585                 590

Ser Ile Ser Thr Ser Glu Ser Val Ser Thr Ser Glu Ser Ile Ser Ser
        595                 600                 605

Ser Glu Ser Val Ser Ser Ser Glu Ser Val Ser Ser Glu Ser Ile
    610                 615                 620

Ser Ser Ser Glu Ser Val Ser Asn Ser Glu Ser Ile Ser Ser Ser Glu
625                 630                 635                 640

Ser Val Ser Asn Ser Glu Ser Ile Ser Ser Glu Ser Val Ser Ser
                645                 650                 655

Ser Glu Ser Ile Ser Asn Ser Glu Ser Ile Ser Ser Glu Ser Val
        660                 665                 670

Ser Thr Ser Glu Ser Ile Ser Ser Glu Ser Val Ser Asn Ser Glu
        675                 680                 685

Ser Ile Ser Ser Ser Glu Ser Val Ser Ser Glu Ser Ile Ser Asn
        690                 695                 700

Ser Glu Ser Ile Ser Ser Ser Glu Ser Val Ser Thr Ser Glu Ser Ile
705                 710                 715                 720

Ser Asn Ser Glu Ser Val Ser Ser Glu Ser Val Ser Thr Ser Glu
                725                 730                 735

Ser Ile Ser Ser Ser Glu Ser Val Ser Asn Ser Glu Ser Ile Ser Thr
```

-continued

```
                    740                 745                 750
Ser Glu Ser Val Ser Thr Ser Glu Ser Ile Ser Ser Glu Ser Val
            755                 760                 765
Ser Ser Ser Glu Ser Ile Ser Ser Glu Ser Val Ser Asn Ser Glu
            770                 775                 780
Ser Ile Ser Asn Ser Glu Ser Val Ser Ser Glu Ser Val Ser Asn
785                 790                 795                 800
Ser Glu Ser Ile Ser Ser Glu Ser Val Ser Asn Ser Glu Ser Ile
                    805                 810                 815
Ser Thr Ser Glu Ser Val Ser Thr Ser Glu Ser Ile Ser Ser Glu
            820                 825                 830
Ser Val Ser Asn Ser Glu Ser Ile Ser Ser Glu Ser Val Ser Asn
            835                 840                 845
Ser Glu Ser Ile Ser Ser Glu Ser Val Ser Asn Ser Glu Ser Ile
        850                 855                 860
Ser Ser Ser Glu Ser Val Ser Asn Ser Glu Ser Ile Ser Ser Glu
865                 870                 875                 880
Ser Val Ser Ser Ser Glu Ser Val Ser Ser Glu Ser Ile Ser Thr
            885                 890                 895
Ser Glu Ser Val Ser Asn Ser Glu Ser Ile Ser Ser Ser Glu Ser Val
            900                 905                 910
Ser Asn Ser Glu Ser Ile Ser Ser Ser Glu Ser Val Ser Asn Ser Glu
            915                 920                 925
Ser Ile Ser Ser Ser Glu Ser Val Ser Asn Ser Glu Ser Ile Ser Ser
            930                 935                 940
Ser Glu Ser Val Ser Ser Ser Glu Ser Ile Ser Ser Glu Ser Val
945                 950                 955                 960
Ser Ser Ser Glu Ser Val Ser Asn Ser Glu Ser Ile Ser Ser Ser Glu
                    965                 970                 975
Ser Val Ser Asn Ser Glu Ser Ile Ser Ser Ser Glu Ser Val Ser Thr
            980                 985                 990
Ser Glu Ser Ile Ser Ser Ser Glu  Ser Val Ser Asn Ser  Glu Ser Ile
            995                 1000                1005
Ser Ser  Ser Glu Ser Val Ser  Ser Ser Glu Ser Val  Ser Ser Ser
            1010                1015                1020
Glu Ser  Ile Ser Thr Ser Glu  Ser Val Ser Asn Ser  Glu Cys Ile
            1025                1030                1035
Ser Ser  Ser Lys Ser Val Ser  Asn Ser Glu Ser Ile  Ser Ser Ser
            1040                1045                1050
Glu Ser  Val Ser Asn Ser Glu  Ser Ile Ser Ser Ser  Glu Ser Val
            1055                1060                1065
Ser Asn  Ser Glu Ser Ile Ser  Ser Ser Glu Ser Val  Ser Ser Ser
            1070                1075                1080
Glu Ser  Ile Ser Ser Ser Glu  Ser Val Ser Asn Ser  Glu Ser Ile
            1085                1090                1095
Leu Ser  Ser Glu Ser Val Ser  Ser Ser Glu Ser Ile  Ser Ser Ser
            1100                1105                1110
Glu Ser  Ile Ser Ser Ser Glu  Ser Val Ser Met Ser  Thr Thr Glu
            1115                1120                1125
Ser Leu  Ser Glu Ser Glu Val  Ser Gly Asp Ser Glu  Ile Ser Ser
            1130                1135                1140
Ser Thr  Glu Ser Ser Ser Gln  Ser Glu Ser Met Asn  His Thr Glu
            1145                1150                1155
```

-continued

```
Ile Lys Ser Asp Ser Glu Ser Gln His Glu Val Lys His Gln Val
    1160                1165                1170
Leu Pro Glu Thr Gly Asp Asn Ser Ala Ser Ala Leu Gly Leu Leu
    1175                1180                1185
Gly Ala Gly Leu Leu Leu Gly Ala Thr Lys Ser Arg Lys Lys Lys
    1190                1195                1200
Lys Asp
    1205
```

<210> SEQ ID NO 3
<211> LENGTH: 5
<212> TYPE: PRT
<213> ORGANISM: Artificial Sequence
<220> FEATURE:
<223> OTHER INFORMATION: Cell wall anchor domain
<220> FEATURE:
<221> NAME/KEY: MISC_FEATURE
<222> LOCATION: (3)..(3)
<223> OTHER INFORMATION: "Xaa" denotes any amino acid residue

<400> SEQUENCE: 3

```
Leu Pro Xaa Thr Gly
1               5
```

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 4
tcacgcaaag ttcgagttaa aa                                    22

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 5
cgcagattta gtagctccta a                                     21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 6
atgtcccaaa agactttgg c                                      21

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 7
cgtcccaaaa gggttgcacc agtca                                 25

```
<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 8
atgtcacgca gtcaaaaagt ta                                          22

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 9
accatcttca agtcgcttac t                                           21

<210> SEQ ID NO 10
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 10
tgatagttac actcaatcaa gtt                                         23

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 11
ctgagtagag cttgaaacat g                                           21

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 12
aaccatggaa ttggttgggc                                             20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 13
aaccatggaa ttggttgggc                                             20

<210> SEQ ID NO 14
<211> LENGTH: 24
<212> TYPE: DNA
<213> ORGANISM: Artificial Sequence
<220> FEATURE:
<223> OTHER INFORMATION: Synthetic oligonucleotide primer
```

```
<400> SEQUENCE: 14
atgacagcct ttaatagttt attt                                              24

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 15
aagatctcca ttctcattga ag                                                22

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 16
cctggtgtct tgatttctgc t                                                 21

<210> SEQ ID NO 17
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 17
ttctcctcat tttcaaatac aga                                               23

<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 18
agctatcgcg ttagcggca                                                    19

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 19
gccttgacca tgataagttg t                                                 21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 20
ggtgcagatt tccaatatcg t                                                 21

<210> SEQ ID NO 21
<211> LENGTH: 21
```

<212> TYPE: DNA
<213> ORGANISM: Artificial Sequence
<220> FEATURE:
<223> OTHER INFORMATION: Synthetic oligonucleotide primer

<400> SEQUENCE: 21
tcatctaaga ggacctactt c                                           21

<210> SEQ ID NO 22
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 22
ttgcgagtac atattacaag tat                                         23

<210> SEQ ID NO 23
<211> LENGTH: 22
<212> TYPE: DNA
<213> ORGANISM: Artificial Sequence
<220> FEATURE:
<223> OTHER INFORMATION: Synthetic oligonucleotide primer[ ]

<400> SEQUENCE: 23
atctataaag catatgcaca gc                                          22

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 24
gataccccct cactatcctt                                             20

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 25
gatattactg atttgagagg gt                                          22

<210> SEQ ID NO 26
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 26
atagatagaa aagatactaa ccg                                         23

<210> SEQ ID NO 27
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 27

```
tgcagctagc tcaaagtcca ataat                                            25
```

<210> SEQ ID NO 28
<211> LENGTH: 24022
<212> TYPE: DNA
<213> ORGANISM: Streptococcus agalactiae
<220> FEATURE:
<221> NAME/KEY: misc_feature
<222> LOCATION: (220)..(220)
<223> OTHER INFORMATION: n is a, c, g, or t

<400> SEQUENCE: 28

```
caaaaacaac tgatagggat tttctaaacc taaattaaaa tcagtatggt aagcccaaat      60
tgtctttaac caatatataa ctactaacaa taaaataaag ccgagtcgtg tattgatcgc     120
acggctagca aaatctttaa ttttttttcac agtaggaact tcctttaatt ttttttcctaa   180
agataaaatc tcagattaaa ttataacata aaattttgtn acatacggta aagaaaggtc     240
gaattcagta tgaaaaaaga taaaaatttg ttataatact gtttatgaat aaacttaaag     300
tgaattctgt cgttgaaaga aaaatcaaat caggtgctca gttactggaa aaaaaagatt     360
ttgataccag tttagttaac cagttggttc aacttttttc acagtcaaat caattcttag     420
ggatggccta tctttcacca caaaataaag ggattggttg ttactatca agacaaattt      480
ttgatttttaa ccatgattac tttgtatcgc tattcgaaaa atctagagag aagcgtcaaa    540
aatttgaaaa atctagccaa acaacagcct accgcttgtt taatcaggat ggagataact     600
ttggtggcct aactatagat ttttatagtg actatgctct tttttcgtgg tacaatgaat     660
ttgtttatac taatcgacaa atgattgttg cagcctttaa gcaggtctat cctaatatta     720
aaggggcata tgaaaaaatt cgtttcaaag gtttagactt tgaaagtgct catttgtacg     780
gtcaagaggc tcctgaatca tttttgattt tagaaaataa tatcaaatat agtgtctttt     840
tgaatgatgg gttaatgaca ggtatttttcc ttgaccaaca tgatgtcaga aaagccttag    900
caactaatct atcagaaggt aaaaaagttc taaatatgtt ttcatacact gcggcttttt    960
ctgtagctgc agctgttgga ggagcattag agacaacttc tgttgattta gcaaaacgct    1020
cgcgtgaact ttcaaaagca cactttgatg ctaatcagat tgtcacagat aaccatcgat   1080
ttatcgttat ggatgttttt gaatattata agtatgccaa aagaaaacat ctatcatatg   1140
atgtgattgt tattgatcca ccaagttttg ctcgaaataa aaaacaaact ttttcggtta   1200
ctaaagatta ctataaatta attgaacaag ctttagatat tttagccccct ggtggaacta   1260
tcattgcatc aactaacgca gctaatctaa ccgtatcaca atttaagaaa caattggaaa   1320
aggggtttgg taaagcttca cataattaca ttagcttaca gcagttgcct gaagatttca   1380
ctgtaaatga taaggaccaa caaagtaatt atttaaaagt atttacaata aaggtaaaat   1440
aatgaaaata gtagtaccag taatgcctcg cagtcttgaa gaggctcaag aaatagattt   1500
atcaaaattt gatagtgttg atattattga atggcgagct gatgccttac aaaggatga    1560
cattattaat gtagctccag ctatttttga gaaattcgca ggtcatgaaa ttattttac    1620
tcttcgtaca acgcgtgaag gtggtaatat tgtcttatct gatgctgagt atgttgagtt   1680
aatccagaaa attaattcta tctacaatcc agattatatt gattttgagt attttttcaca   1740
taaagaagtt tttcaagaaa tgctagaatt tccaaattta gtcctgtctt atcacaatt    1800
tcaagagaca ccggagaata ttatggagat attttcagaa ttaacagccc tagcaccacg   1860
agttgtgaaa atcgcagtaa tgccaaagaa tgaacaagat gtcttagacg ttatgaatta   1920
cactcgcggt ttcaagacta ttaatcctga tcaagtttat gcgacggtat ctatgagtaa   1980
```

```
aattggacgt atttctcgtt ttgctggtga tgtaactgga tctagttgga catttgcata    2040
tttagattca tctatcgcac ccggacaaat tactatttca gagatgaagc gtgtcaaagc    2100
attgcttgac gctgactgat acgagataac aaaatgttaa atatactgat gagatcccta    2160
gcaattgctt agggttttg tcttattaaa acaaacatga gaggacatta gaatgcaggt     2220
tgaagttgac ttaccgaatc acccttatca tattaaaatt gaagaaggat gtttttctga    2280
ggctggtgac tgggtatcac atttatggca gaaacaaatg ataactatta ttacagatag    2340
taatgtagaa atattatacg gggagtcgct tgtcaaccag ttaaaaaaac aaggttttac    2400
agtacatgtt tttagttttg ctgcgggtga agctagtaaa actttggaag ttgctaatcg    2460
tatttatggt ttttagcaa agcatcatat gaccagaagt gatgggatca ttgcacttgg     2520
tggaggcgtc gtcggagatt tagcagcgtt tgttgcttct acttatatgc ggggaatcca    2580 tttctcttcaa attccaacta gtttaacagc acaggttgat tcttccattg gcggaaaaac    2640
aggagtcaac acttcattcg ctaaaaatat ggtaggtact tttgcacaac ctgatggtgt    2700
actgatagat cctgttactc taaaaacatt gggcaatcgt gaattagttg aaggtatggg    2760
agaagtcatc aaatatggct tgattgatga tataaaactc tggcatatct tagaagagat    2820
ggatgggtct attgatagta tccttgataa tgcattagct attatttatc actcttgtca    2880
agttaaacga aagcatgttt tagctgatca atatgataaa gggttaagga tgcatttaaa    2940
ttttggccac actatcggtc atgctatcga agtacatgct ggctatggag aaataatgca    3000
tggagaagct gttgcaattg gaatgatcca gctttctcgt gtggctgagc gtaaaaatct    3060
tatgccaaga ggtatcagtc aagatatttta taatatgtgt ttaaaatttg gccttccggt    3120
ccactatgca gaatgggata aggacgtctt atttaacata ttgagtcatg ataaaaaagc    3180
aagtggacaa tttattaaaa ttgttatact gcctcaatta ggtagtgcaa cagtccacca    3240 aatacccttta aagaaatga gagattattt ggagaaatag atgagatatt taactgctgg    3300
tgagtcacat ggacctagtt taacagctat tatcgaaggg attcctgcgg gactgaaatt    3360
atctgctaaa gatattaatg aagatttaaa acgccgccaa ggtggttatg gtcgtgggaa    3420
tcgaatgaaa attgaaactg atcaagtgat cattagttct ggtgtgcgcc atggaaaaac    3480
cttgggttca cctattacac tgacagtaac taataaggat catagcaaat ggctggacat    3540
catgtcagtc gaagacattg aagagcgtct aaagcaaaaa cgtcgtatta agcatcctag    3600
acctgggcac gcagatttag taggtggaat caaataccga tttgatgatt tgagaaatgc    3660
tttagagcgt tcttcggctc gtgagaccac aatgcgagta gctattggtg cgattgctaa    3720
acgtatcttg aaagaaattg gtatcgaaat tgctaaccat attgtagttt tcggtggcaa    3780
ggagattact gtccctgata agctaacagt tcaacaaatc aaagtgttat ctagtcaatc    3840
gcaagtagct atcgtcaatc catcatttga acaagaaatt aaggattata ttgacagtgt    3900
gaaaaaggct ggagatacta tcggaggagt gattgaaact atcgttggag gagttcccgt    3960
tggtttaggc tcttatgtac actgggatag aaagttagat gctaagatag cgcaagcagt    4020
tgtatctatc aatgctttta aaggtgttga atttggtcta ggttttaagt cagggttttt    4080
aaaaggaagt caagtaatgg actccatatc atggacaaag gaccaaggtt acatacgtca    4140
gtcaaataat ttaggcggtt ttgaaggcgg tatgactaat ggagagccta ttgtcgttag    4200
gggagtaatg aagccaattc ctacgcttta caagccacta atgtcagttg atattgatac    4260
tcacgagcct tatagagcta cagtggaacg ttctgatccc acggcacttc cggctgcagg    4320
```

-continued

```
tgtcgttatg gaagctgtag tagccaccgt cctggtgaca gaagtgctag aaaaattttc    4380
ttcagacaac atgtatgaac taaaagaagc tgtaaaacta tatcgcaatt atgttaatca    4440
tttttaagtg aaaactagta gcattcaatt gcaaaaaaag gtataaaagt ctacaatagt    4500
ggtaagttca agtagaaaaa ggagtaactt atggctaatg tatatgattt agcaaatgaa    4560
ttagaacgtg ctgttcgtgc tttaccagaa taccaagcag ttttaactgc aaaagcagct    4620
attgaaaatg atgcggatgc acaagtgctt tggcaagact ttttggctac ccaatcaaaa    4680
gttcaagaaa tgatgcaatc tggccaaatg ccaagtcaag aagaacaaga tgaaatgtct    4740
aaacttgggg aaaaaattga atccaatgac ttttttaaaag tttattttga ccaacaacaa    4800
cggttgtctg tctatatgtc tgatatcgaa aaaattgtct ttgcacccat gcaggacttg    4860
atgtaatagt ataaaagaga gagctccttg agttttctct tttatgctat ttacattcag    4920
agcatcctaa ttgctgcgct tttacattat tgcattatcc tataaaaatg tatttttata    4980
cttttttgag agcggctatt tattttttaga cttagtcatg tctctaaata cccctagtta    5040
gtgataaaaa caaggttttt ataggataag gaggtaagaa tattaaaata taaacatcat    5100 aaatattttat attttgtttt tttataataa aaatgtgttg tagattaaat tataaaacca    5160
gaaaactaat tttatatttt ttataattta ctgaaaatta acatataatg atgatagtga    5220
tttgaaatat acaatagtag cgaagaagaa cactatgaaa tactttgaat aatagtagta    5280
aaaaataagt gttaaaaaaa ctgaaatttt atatccaatt tgattaaagt atgttataat    5340
acgaaaagtg ttttttaaaaa caccttattt agattagaaa gaagcaatag ttgatttaat    5400
tttcagaaga gaggaagaat tgtttattgt agcttttttaa gataggaggg gtctttatag    5460
gcaaatatgc tatttattga tgatgtttca agcaatattt tagaacttga ataacaaag    5520 tagtatttttg ttatagctat atttgagaat tcttagaatt agaaaagttt tttatatagc    5580
attatttttt aaatatggag gaaaaatgtt aaaaaagcag tttggaaact ttggtgaaaa    5640
atcacgcaaa gttcgagtta aaatgaggaa atcaggtaag cactgggtca aaagtgttat    5700
gacacaaatt ggctatgtta tccttttcgag gtttagcggt aaagagaaaa gctctaaggt    5760
tcaaactact agtgaagatt taagcagaac taaaacgtct gctagcatcc taacagcagt    5820
cgcagctctt ggagctgtag ttggagggac gacagacaca acttctgtct cagctgaaga    5880
aacacctact gcaacagaac ttacaggaaa tgaaaaaaca ttagctactg ctgaaactgt    5940
agtggttgcg ccagaagtaa aaactgtaaa ctcagattct tcatcacatt caacaagtga    6000
atcacaatca atgtcaacta gtaccttgca atctaccagc gcctcattat ctgccagtga    6060
atcactaatg gattctacct ctgcttcttt atctgagtct agctcgttat cagaatatag    6120
ttctttatct ctatctagta gtgagagtgt ctcagcatca gaatcagttc aatcatcaga    6180
agcggcaacg accgctagag ttcaaccgag agcgatgaga gttgtatcta gtgcttcaga    6240
tatgaaaact ttaccagcag cattaatctc tggtgaagga gatgtaacaa ctgttcaagg    6300
acaagatgta acagataagt tacaaaattt agatataaag ctctctggag gagtgcaagc    6360
aaaagcaggt gttataaata tggataagtc agaaagtatg cacatgtctt taaaattcac    6420
tattgattct gtgaatagag gtgatacttt tgaaattaag ttatcagata atatcgatac    6480
aaatggagct tctaactatt ctattgtaga acctataaaa tcacctacgg gtgaggtcta    6540
tgcgactgga atttatgatt ctcaaaaaaa atctatagtc tatagtttta cagattttgc    6600
ggcttcaaaa aataatatta atggaatatt agatattcca ttatggccag atgatacgac    6660
agttcaaaac acaaaagaag atgttctttt ttcggtaaaa ataaaggatc aagaggctac    6720
```

```
aattaaagaa acagtgaaat atgatccacc ggtaagaatt gattttgcag ggggagtaag    6780
tgtagattct cgaataacca acattgatga tgtgggaaaa aagatgactt atataagtca    6840
aattaatgta gatggaaaat cactctataa ttacaacggg ttatatacta ggatatataa    6900
ttatagcaaa gagagtacag cagatttaaa gaattcaacg ataaaaatct ataaaaccac    6960
ctcggataat attgtagaga gtatggtaca ggattattca agcatggagg atgtaactag    7020
taagtttgca aatagttacc cagaaaaagg gtggtatgat atttattggg ggcagtttat    7080
tgcatcaaat gaaacgtatg taattgttgt agaaacacca tttactaatg cagtaacttt    7140
gaatactact ttatcagatt ataatgagaa caatggtgta gaacataatc atacttactc    7200
atctgaatcg ggatattcag atgtaaatgc tcaagaaaga aaaattttat ccgaattagt    7260
aagtagctca gaatcagtat caagttcaga atcggtatct aattccgaat ctatttcaac    7320
ttctgaatcg gtatctaact ccgagtctat ttcaagttcc gaatcggtat caagctcaga    7380
atctatttca acttctgaat cggtatcaac ttcagagtct atttcaagct ccgagtcagt    7440
atcaagttca gaatcggtat caagctcaga atctatttca agttccgaat cggtatctaa    7500
ctccgagtct atttcaagct ccgaatcggt atctaactcc gaatccattt caagttctga    7560
atcggtatca agctcagaat ctatttcgaa ttcagagtct atttcaagct ccgagtcagt    7620
atcaacttca gagtctattt caagctccga atcggtatct aactccgaat ccatttcaag    7680
ttctgaatcg gtatcaagct cagaatctat ttcgaattca gagtctattt caagctccga    7740
gtcagtatca acttcagagt ctatttcaaa ctccgagtcg gtatctagct ccgagtcagt    7800
atcaacttca gagtctattt caagttccga atcggtatct aactccgaat ccatttcaac    7860
ttccgagtca gtatctacct cggaatctat ttcaagttct gaatcggtat caagctcaga    7920
atctatttca agttccgaat cggtatcaaa ctccgagtct atttcaaact ccgagtcggt    7980
atctagctcc gagtcagtat caaattcaga gtctatttca agttccgaat cggtatctaa    8040
ctccgaatcc atttcaactt ccgagtcagt atcacctcg gaatctattt caagttctga    8100
atcggtatca aattcagagt ctatttcaag ttccgaatcg gtatctaact ccgagtctat    8160
ttcaagttca gaatcggtat caaattcaga gtctatttca agttccgaat cggtatcaaa    8220
ttcagagtct atttcaagtt cagagtcagt atcaagttca gagtcagtat caagctcgga    8280
atctatttca acttcagaat cggtatctaa ctccgagtct atttcaagtt ccgaatcggt    8340
atctaattct gaatctattt caagttccga atcggtatca aattcagagt ctatttcaag    8400
ttccgaatcg gtatcaaact ccgagtctat ttcaagttcc gagtcagtat caagctcaga    8460
atctatttca agttccgaat cggtatctag ctccgagtca gtatcaaatt cagagtctat    8520
ttcaagttcc gaatcggtat ctaactccga gtctatttca agttccgagt cagtatcaag    8580
ctcagaatct atttcaagtt cagaatcggt atcaaactcc gagtctattt taagttccga    8640
atcagtatca agctcagaat ctatttcaag ttcagaatct atttcaagtt cagagtcagt    8700
atcaatgagt actacagagt ctctaagtga atcagaagta tcaggggatt ctgaaattag    8760
ctcaagtaca gaatcatcaa gtcaatctga atcgatgaat catactgaaa ttaaatccga    8820
ttccgaatct caacacgaag ttaagcatca agtattacca gaaacaggtg ataactcggc    8880
ttcagcatta ggtctgttag gtgcaggatt gttgttagga gctactaaat ctcgcaagaa    8940
gaaaaaagat taattttcaa agtgatattt agatgataaa tcgaaagtac tttcgattta    9000
tcacttaaga tagtaagtag ttatactgtc ttaagtgata aattgatttg aaaagggaaa    9060
```

```
aaatgattgg aaaattatat tatagctata gaaagtcaac gctattaaga agtattttat    9120
ggactatttt aattgttggt gtatatatgt taggacaacg tgttttatta tccactgttc    9180
ctttatcaca tcaagagata aaactagcag tagatcaaca tttactcaat aacttttcag    9240
cagtaagtgg tgggagtttt aataaattaa atgttttcac actggggttg agtccatgga    9300
tgtcaagtat gattatttgg agattcgttt ccttattttc gtgggcaaaa aatgcaacga    9360
agcgaaaagc agaagtagct caatatactt taatgcttac tatctcagtt atacaagcat    9420
atggtgtttc aggaaatcaa tttataaaaa gctctttatt aggttcttat agtgatattg    9480
tttttaaagc attgacaatg gtcttgttaa taagtggctc atttgtgtta atgtggcttg    9540
ctaatctcaa tgcttctaaa gggctaggag aagtattgt tatcatatta gtgagcatgc     9600
tccaagcaac gactactgga ataataactt attttgaaca gtcacatttt agtattatgg    9660
atctgctggg aactattata gctataagta taatacttag tgttttatta ttaatctcaa    9720
cggtggttta tagggcagaa tatcgtatac ctattaggcg tattgatatc gttagtaaat    9780
ttgcccaaga tacctatatt cctattcgca taaatccagc agggtcctac cctttcatgt    9840
atgggatgac attaatgatg cttccaacgt ttataattca agcattgtta cttgcttttc    9900
caaacgagcg attattgatt cagatctcgt caatgattgc aattaataag cctttaggta    9960
ttggactttt tgttatatta ttatttattt tgagcattgg atttgcatat tttaattacg   10020
acccgtataa tattgcaaaa aatatgcgtc aacgggggga atattttcaa aatgtaactc   10080
caggagctgc tactcaacgt tttttacaag aaaaaattag tatcatggca gtagttggag   10140
caatttttac ggttattatg ggaggtctcc caatgttggc tgtggtgggg aagacaaacc   10200
aagttagtat tgcaatgatc gtcattaata tttatattat ttcaactttt atgctcagta   10260
ttattgagca agttaatacc ttgaagttgt ggggcagtca ccgaaatatt atttaaggag   10320
caatcatgtt ttattttatt ccttcgtggt acaattctga tcaaaagtgg cataatgaag   10380
ctcctatctg gtatcgtgta ttggagaaca tgacttttga tgatactgtt agtcaggtta   10440
gaatgtttca gaatgcagat gaggaagtgc gtttacttct atttagttat aatcctcagt   10500
tgagatacat gcttcatgaa gagagtatgt tggctgtctc ttattggtct ttttttgacg   10560
atattcaaaa tattcaacaa aaagagatta agttaattaa ttttaaagaa ctgaattggc   10620
ctaaagggac ttattttgtt tatacaccctt ttttagtatt agctaaacat ggtggcgaga  10680
ttattgcacg tatccaattt gcggaaaatg ggaattact actgattgaa cttttaatag   10740
atggtgtgct tgataagatt atgatatttg acgatcgtgg ttttgtatcc agtatcaaat   10800
atttcaaaca aaatagatta atttatcaag attatttaaa tcaaatggt gtttggcaaa    10860 ttcgagagta tgcttcaaaa tttccgagaa tagtagttaa tccaatgtct gataaggtgt   10920 ttaatttttac tgagtatgat gattgggata ctcttattcg agagagaata ttggttttaa  10980
aaaaactaga agtgactcca gatgattata ttatagtagc agtaaacgat attcataaca   11040
atttagtcag aaaatcattt ccagatcaaa agaaaatttt ctcatttttt ggtgaacgct   11100
attcatttga taatcgactc gactttaatg aacttcttga tgaaggtgaa ttgtttattg   11160
ctgaaagcga aaaatagaa cggttattga ttacttcatt acaagagaaa aattattcgt    11220
caaactatgt tgagaatcac attagccgta ttcccccttt tgatactcgt ttgagactcg   11280
gacagagcca aaatattgaa gagcttattg catatttact tgtagatgat cttttctcaaa  11340 cttatttaag tgaagttta gaccaattat tagcaaaaat ggaagttaat ccgtcattag    11400
agttgaaaat agtcagctat aaaaatgatt atgatatgac ttctctaaaa gaacaagtta   11460
```

```
aggacaaaat attgtcttct aaaaatccag attattttt tacctctctt tctttggaag   11520
atgagaatca ttttaaggaa gaacaaaaaa ctaaaattcg tggcattagt tttgatatat   11580
atacaaatga aaatcaaatt atagatgctc tagatactgc taggttagtt attgatttaa   11640
gagatgatcc agacctatat actcaaattg ctgctctgag ttctggaatt cctcaaatca   11700
ataaagttca cactaattat gtagaacacc agaagaatgg ctggattatt agtgactcta   11760
cagaactcaa taatgcaatt gactattatt ttgatggact aatgaattgg aataaatcgt   11820
tagtttacag cgtaaaaaaa atgggtgatt atacaagcgg taagatatta cagcgctggc   11880
gaaaattatt agaaaagaa taatatggaa aaattaaaaa ttttgcagat tggtgaggaa   11940
ccatgggatg ctgatttaat aactccagac aatattgaat ggttatactg taatggaaat   12000
gctattcaaa ttttcttaga gaaattaaaa agtaaagagt tagaaaaaaa taatgttgaa   12060
tatattggta aaacttcaac taatgaagtt aaattatggt ttaatgcggt cattttaact   12120
agtgaggtta gcgaattgca attgaaccta ctttcagatt gcttagaagc gcatacactc   12180
ttttacgacg aggattttca actcgatttt tgctcagaaa acggtatatt taaacgtaag   12240
gttttgagac cactaccatt taatggatca aggaaagaaa aaattatttt cctaagccgt   12300
actctttttt cggaacaata tggtgcaaaa ttgaaggttt ctgacataga tctaaatcct   12360
gattttaagg gagagataat atatgaaggc aatagctcta tttgtttttc agggaatttt   12420
ggagaagatt ttcaacctct attctcattt cgctataatt tatcctctac tgataaagcg   12480
atagaaatat ggcaagaata tcaaaaattg caaggtgata atagtattat gatagaagtc   12540
attcaatacc aaaaaggatc acttgatttg atattaaata caaaataccct ttcagaaaaa   12600
gatttggctg atccatatat tttagaatat gatgaatcag ttggttttc atcaatttct   12660
atctttgcta gaggtgacgg agtggtgaga tttggtgcac tacattggcg atattcgcgt   12720
aaaggtttgg gtcaattttt aatcggtgga gaaaggtaca gtgattccaa aaggcaagag   12780
tttatctact atttaaccc aggagatatg aaacctccat tgaatgttta ttttcaggt   12840
tttcgaggag ccgaaggttt tgagggtttt tacatgatga aacgtttggg agctccgttt   12900
ctcttaattg gtgatccaag gattgaaggt ggaagcttct acctaggtac ttcagaatac   12960
gaaagtgaat tagaaaatgt tttacaaaaa tatttagatt acctacaatt tgatcattgt   13020
caacttattt tatcaggttt atctatggga agttttggtg ccctttatta tagttctact   13080
ttttccccc atgctatagt tgtggggaaa ccctttacaa atttaggcga tatggtagta   13140
aatttaaaat taagaagacc agatgatttt tgaaacgagta tggatattct ccaaaatatt   13200
attggttctc aaaacgatga agctattaat caatttaatc aaaaattttg gaataagttt   13260
aagcgttcta attatgaaaa aacgcagttt gctatatctt atatgaaaca tgatgattat   13320
gatagaaatg caactccaag gctgattgat tattttttcta aaactaacac cctgttgtat   13380
gcaagtggat atgctgggcg acataatgat aatagtcaat caataaataa ttggtttact   13440
tctcagtata aaacaattct cagtgatgat tttgggagag tgtttagtgg ttaaaaaaag   13500
aatacagaag gtgctttgga ctgatagtag caatgtttat ctttatggtt cgactataaa   13560
gtatttggag cataatcgtg tttttttga gaatctaaga ttctctacag gaaaacaat   13620
caaaaaatgg ctttctaaaa cgaattttca agctaataga acgttgccag agcttacctt   13680
actaaaacct aatcatacct atgagttggt atcaaaatta actactgtgc ctgagggatg   13740
cgtgattatt cagataaatt tttataatcg tcaaaaagaa aaaataggtt tttctattat   13800
```

-continued

```
tcgagatcac tcctcagatt ttatagttcc tgatgacaca tattttatg atatttctct    13860 tattggtgcg ggttgtataa gtgtagaatt ttgttaccta gaattatttg aagtaattga    13920
gactcaagaa gaaaaagatg gtattgaact aaacagttat gttgaaagca gcttaccatc    13980
agagcttgaa cttattagaa cgttgatagc attttctaag gataaaaaat gaaaaaagtt    14040
gttgttaaac ccaaaatctc tattctaaat aaattgagat tgcaaagaat tcaaaaaatt    14100
gtaaacgaga taaataataa aaaagtgtac tacgctcaat tatcagataa ggagttaagc    14160
catcaaactt taatattaaa aaatagactt tcaagtggag aaagtctaga tgatattctt    14220
gttgatgctt ttgctgtgat aagagaggct aataaaagaa ttttaggttt gtttccatat    14280
gatgctcagg ttatgggtgc tattgctctt catcaaggaa cgatagctga atgaaaacg     14340 ggagaaggaa aaacattaac tgcaactatg cccttgtatc tgaatgcttt aactagcaag    14400
ggagcaatct tagtgacgac caatgattat ttggcaaaac gagatgcatt agagatggga    14460
aaagtatatc aatttctagg tatgacagtt ggtattaatg tttttgataa aaagaagaa     14520 gcagatgcga ctattaagag agaagtatat gaatctgata ttacttatac tactgcaggt    14580
gccttaggtt tcgactatct cgttcacaat ctggctagta taaactaga acaatttcta     14640 agaccttttc attttgttat cgttgatgaa gcagactctg ttttgttaga tattgctcaa    14700
acacccttaa ttatagcggg agatcctcgt gtacaatcta atctctatgg tatcactaat    14760
aattttgtac tcactcttaa ggaaaatgat gaatatatcc ataaagctaa ggataaaatt    14820
gtctatctta ctgagaaggg tgtaagttac gcaaaacagt acttcaatat ttcagaatta    14880
tataatgatg agtattggga attaaataga catataaacc tagcattgcg tgctcattgt    14940
ttgtataaaa gagattatga ttatgtagtt aaaaataatg aagtaaaatt gttagataac    15000
gcaacaggtc gtgttatgga aggcacaaaa cttcaatcag ggattcacca agctattgaa    15060 gcaaagaag atgttgcttt gacaaatgaa tctagggcaa ttgcttcaat aacgtatcaa     15120
agtctcttta atatgttccc aaggttgtct gggatgacag gaactggaaa atcttctgaa    15180
gatgaactta taaaaactta ccacctgcct gttattgtta taccaacaaa ttttccgatc    15240
aaacgagtag atcttgccga taaaatatat gttagcttac cagaaaagtt gcaagctact    15300
atagatgatg ttaaacaaag acatagtaaa ggtcagccag tattgttaat ttctggaaca    15360
gttgaaattg ctaacattta ttcaaagtta ttgctgcgag aaggcattgc ccataatacc    15420
ttaacagctg ataatgttgt taagaggca caaattataa agaagcggg acaaaaaggt      15480 tcagtaacat gtgcaacagt tcttgctggt cgtggaacag atattaaact aggtgaaggg    15540
gttagagaat taggaggact tgcagttata ggaacggaaa ggatgcctaa tttacgtatg    15600
gactggcagc ttaggggccg ttcggggcgt caaggagacc cagggattag ccaatttat     15660 gtgtcgctag aggatgaatt aattgttttct cattctccgg aatgggtgat aaagtattta    15720
aaaaaatatt ctcgtaaaga aacttcaaat tactatatgg tacctagaaa gaaacgcttt    15780
ttttatcaaa tagttaaaaa tgctcaactc agaagtgaag ataaaggtgt atcttctagg    15840
gagcaaacta ttaagttcgg agagagcttg cgtatacagc gtgaaaatat ttatcaatta    15900
cgaaatgaat taatagctga tagttccatt gtggttgatg gtgtgataaa aattattcag    15960
gataatttta acgatattgc taatgataag gatttaacgg aacattcttt acgaagatat    16020
atattagaaa atcttaccta taaatttaaa tatttccctg atgaatttga cgttcataat    16080
tctgacgatg tatttaaatt attgattgac atatttgata gagaatttac tgcaaagaaa    16140
actaaacttc aaagtgataa tgaatttgat aatttcgtca gaatatcgat attaaaggct    16200
```

```
attgacaaat cgtggataga agaagtggat agcctacagc aattaaaggg agttgtaacc   16260
aatagaggta tcggtcaacg agatattatt caagaatatt ataaagaatc gcttaattct   16320
tactataaga tgggaaaaga aataagatat tctatcgtta agaatattat gttaagtaca   16380
atttcaaaag caagtgatgg aagttactca atatattatg tataaaggaa aacggagtta   16440
atggtagttt ataatttgaa tagagggata ggttgggcaa gtagcggtgt agagtatgct   16500
caagcatatc gttcagaagt ttttagaaag ttaggtgttg aagctaaatt tatttttact   16560
gatatgtttc agaatgaaaa tatagagcac cttactcgaa atatcggctt tgaagacaat   16620
gagattatat ggctttatac ttttttttact gatttaacaa ttgctgcaac ttcttattca   16680
ctgcaacaat tgaaagaaag ttttttcacta ccgattgata ggactgagaa aaacggtaaa   16740
ataatatcat ttttttttaa aggaagtagt attgtagtta cagttatgct taacgatgaa   16800
tctagtaaca tcgtccaaag ggtagagtat cttatggggg gaaagcttgt tagaaaagac   16860
tactactcat atactaaaat gttttcagaa tattatgctc ccgaagatat aggtccatgc   16920
ctgtatcagc gtacattta taatgaagat ggaagtgttg catatgaaga aaatgtagat   16980
ggcgagaata gtattttttaa attcaaagaa actatactat attctaaaga agaattagtt   17040
ggatacatgt tagaaaaatt acaattaacg aatagtgatc taatcttgtt agaccgctct   17100
acaggcattg ggcaagctgt tctaaggaat aaaggaaatg ctaaagtagc tgttgttgtt   17160
catgcagagc attataatgt tagcgcaact gatgaaacta cgattttatg gaataattat   17220
tatgactatc aattttcaaa tgctgatagc ataagatgctt ttatcacctc aacagaaacg   17280
caaactaaga cgttgattga tcaatttaaa aagtatttaa atattgaacc ggtcgtttat   17340
acaattcctg taggaagttt atcaaaatta cagagaaaag agtggcatga aagaaaagct   17400
ttttcgttgt taacttgctc acgtctagct tcggaaaaac atattgattg gttaattaat   17460
gctgtggtag aagctaataa agtaattcct gaattaacct ttgatattta tggtgaaggt   17520
ggcgaacggc aaaagttaca agaaataatt gctaaaaata aggcaaataa ttatatacga   17580
ttaatggggc ataaaaacct atcttctgtt tataaagatt atcaagttta tttatcgggt   17640
tctaccagtg aaggttttgg tttaaccttg atggaggcaa tcggatcggg gcttccgata   17700
attggtttag atgttccgta tggtaatcag acctttattg aaaataattt gaatggctac   17760
cttattccaa gggaaacacc agataatcct caacaaatat caactgcttt tgctcagtat   17820
attgttgctt tatttaattc taaagatatt tgtaaaaaac acgagtattc ttatagaata   17880
gctagtagat ttttaaatga taaaattata gaaaattgga gttttttttt gaggaggtta   17940
ttaaatgatt atactatttg atttctttga taagaaaagc aaagatctat attattcttt   18000
aattacttca ggtttacatg gaaatgctgt ggtcattaat gacgatggtt ttcttccaca   18060
aaatataaat tctccttatt cattttttttg taatatggaa gggaaaaatg ggaatcctct   18120
ttattttaac caagtcccac tccctgacct ttgggagata aagggaaata atatagaggc   18180
tgaaatttgg gatttttagta ttaaaagagc taaaattttt tatcaagagc cgaagtataa   18240
acgtcaagta aaaaatattg attggtttga caataataaa aaagtgagat acacagatca   18300
ttataatcgc ttcggatggt gttttgcacg tacacattt gataagaatc aaaatgtgac   18360
tacaaaatct tatttcgata aggatggtaa agaagttatt gttgaaaatt ttagaacagg   18420
agttataatc cttaattggc taaataaaga ttatttttttt gataatcgag ttgcattctt   18480
aaatttttat tttagcctta tgggttggaa cttgtctcga atatggtaca actccttatc   18540
```

```
aactccattt ttcgtttctt accggatgac ttatccagga gaagatattt tattttggca   18600
agaagatata gaggatacta ttcctgctaa tatgcgcgtg ttattagaaa gtacgaatac   18660
tagaactcag aaagtaattg ttcaaaagaa aaatacatat cataaaataa agtcaatgtt   18720
acctaaagaa caacaagaaa aaattggtta tttaggcttt atatatccta ataaaaagaa   18780
caataagggt aggaaagata ttttttatttt gacaaactct gaccaaattg aacatttaga   18840
agtgttggtt catcacttgt ctgattatca ttttcatatt gcagcgtaca cagaaatgtc   18900
ttttaagttg atgtcattta gccaagaaca aaatgtaacg ctatatccga atatttcaag   18960
aactgattta gacaacttat ttgaaatctg tgatatttat tttgacatta atcatggaaa   19020
tgaagttgat gatgttatta gaagggcatt tgaatataat caccttatct ttgcttttga   19080
taatacctgt cataacagag agttagtatt agatagcaat atcatttctc acacaacctg   19140
tgaacaattg ataaatttaa tgaaaaattt atcaggctcc attatgtatt gctagagca    19200 acaaagagaa caaacaagta atgaaacaaa agagcgttat aaagaaatat taggaggta    19260 tggaaatgcc taaagaaat gaattactca ataagaaat taaatgagt attgataaac      19320 ttagatataa agaaccagag agtgaacatg acaagcgacc tacttttat ttggtagtac    19380 ttatacttgt tactgtagca gttatattgt cgttatttaa atatttttta tagattccta   19440
ttaatggtag aaaagaagcc tgttgttttt tagataggg aagtgtgtga ggacatatat    19500
tacaaacttg aatggacatt caatcactag tacagcacaa atagctcaaa acatggtaac   19560
agatatagca gtaagcttag gttttcgtga gctgggaata cattcttatc cgattgatac   19620
tgattctcct gaggaaatga gtaagcgttt agatggaatc tgttccggac ttagaaaaaa   19680
tgatattgtc atatttcaga cacctacatg gaacactaca acttttgatg aaaaattatt   19740
tcacaaatta aaaatatttg gtgtaaagat tgttatttt atacatgatg ttgtaccgct    19800
aatgtttgat ggaaatttt atttgatgga tagaactata gcttattata atgaagcaga   19860
tgttttaata gccctagtc aagcaatggt cgataagctt caaagttatg gcttgacagt    19920
aaaaaaaatc ttagttcaag gaatgtggga tcatcccacc aatattactt tacaagcagt   19980
taatcataag aagcttgttc attttcctgg gaacccagag cggtttaact tcataaagaa   20040
ttggagaatt cctaccgagt tacatgttta tactgaccat aacatgcaat tacccaccac   20100
tgtggttaaa gagccatatc aatcggacga acaattaatt atgaaaatga gcgaaggggg   20160
atatggctta gtctggatgg atgaccgtga taaacaatat caatctcttt attgcccta    20220 caaactgggc gcttatatag cagcaggaat tccagtgatt attcaaaaag gtattgctaa   20280
tcaagatata atagaaaaaa ataatttggg atttattatt gaaaaaattg atgatattag   20340
taatatagtt gaaagtacta ctgaagagga atatatggaa attgttagcg atgtcaggcg   20400
gtttaatcct ttagttagac aaggatattt tacgcgaaaa ctattaaccg atgcagtatt   20460
tagtgcatta aatagcatgt gaggggaata tgaaagaact agaagaaatc gtagttttcc   20520
ctataaacaa agtttggat tacattttgg aaaatcattc gtcagttatt cgctttgggg    20580
acggtgaatt tgacattata atgggaaaat cgattcctta tcaagattac aacccagagt   20640
tagcagatag gttattgcaa cttcttcata agcaaagtac gaatgatcta ttagtatgtc   20700
ttccagatat gtttcaaaat cgacaaagat ataatcaatc ggcacaactt ttttggaaaa   20760
atcattttca aaaatttggc aatttctata ggcaacattg ttatcaagat tggtatggtt   20820
cttcttttat ttcaaggcca tatatggact tacaagataa ggagtctgct gtagaatcat   20880
ttaaaaaatt aaagttactt tgggacaaac gcgatatttt ggtagttgaa ggggaaactt   20940
```

```
cgcggtcggg tgtaggtaat gatctttta ataattgcaa tagtttaaaa aggattattt    21000
gtccttctaa aaatgcttat ataaaatatg atgaaattct tgaggctgtt gaaagatatg    21060
ctcaagggag gataatctta ttgatgctag gtccgactgc aaaaatttta gtaagagatt    21120
tatctgatag aggatttcaa gccattgata tcggtcatat tgtttctgaa tatgaatggt    21180
ataagatggg agctactcaa aaataaaat tttctcataa acacaccgct gagtttaacg    21240
atgatgaaaa tattaattta attgacagtc agaattatat tgatgagatt gttaaaacaa    21300
taactatcga tgatactgaa ttcagggata ctgaattaat atcaatcata cttcctgtct    21360
ataatatgtc tggttcttta tcaaggtgtt tagattctat ccttaggcaa gtttactcaa    21420
cttttgaggt gatcttagtc aaccatggtt ctacagatgg aagtggtaat atttgcgaga    21480
aatatgcgat gaaggatgag cgtattcgtt tatttcatga agaacatcaa gttattacat    21540
ctgtatggaa cttcgcatta gagaaatcta agggaagta tgttactttt gtgaatccag    21600
atgattttct tgatgagtct tacttaaatt atctttacaa taaattaaga gctaataaat    21660
ctgatatctc agcaaccacc tatactttt ttaatgaaga ggaaaaatgc tttgtttatt    21720
ttgcaacaga tgataattat tttgagaaaa cattctttgc tcaagaatgg ttagagcaag    21780
aacatagtta ccacgataat ttaaaacaaa tatttcctct cctttctatg aagctcttta    21840
gaaaatcact ttttaacaat atcacttttc ctttagaaga tttaacagga gaatacacac    21900
tgtataatgt ttatttgcta tcaaggcaca ttacattttc tcatattggt ttatacataa    21960
cctctcaagt tttctctcat actgaaataa aaagattcac gggacatgat atagagaaga    22020
tgctatctag aaaggaagag aggttagccc tgttaacaat ggtagggttt aattctgaga    22080
aatacatcaa aaattataag gaaactttat taaattatca aagtgagtcg ttgaatatag    22140
gtgatattaa tttatataat aaaattaagc aaaagattgc attgatagat tattgttact    22200
agaaataatt ttaacagcaa gttaggatat gataatcggt aatataaatt gtttacgtag    22260
cagaaaattg tgactgtaaa cactttgtga tagagtatag gtatcaatga ttcaaggaga    22320
gagtaatgtc aaaacaatat gattatatcg ttattggtgg aggtagtgca ggcagtggta    22380
ccgctaatag ggcagccatg tatggagcaa aagtcctgtt aattgaaggt ggacaagtag    22440
gtggaacttg tgttaactta ggttgtgtac ctaagaaaat catgtggtat ggtgcacaag    22500
tttctgagac actccataag tatagttcag gttatggttt tgaagccaat aatcttagtt    22560
ttgattttac tactctaaaa gctaatcgcg atgcttacgt gcagcggtct agacagtcgt    22620
atgccgctaa ttttgagcgt aatggggtcg aaaagattga tggatttgct cgttttattg    22680
ataaccatac tattgaagtg aatggtcagc aatataaagc tcctcacatt actattgcaa    22740
caggtggaca ccctctttac cctgatatta ttggaagtga acttggtgag acttctgatg    22800
attttttggg atgggagacc ttaccaaatt ctatattgat tgttggggcg ggctatatcg    22860
cggcagaact tgctggagtg gttaatgaat taggcgttga acccatcttt gcatttagaa    22920
aagaccatat tctacgcgga tttgatgaca tggtaacaag tgaggttatg gctgaaatgg    22980
agaaatcagg tatctcttta catgctaacc atgtacctaa atctcttaaa cgcgatgaag    23040
gtggcaagtt gattttttgaa gctgaaaatg ggaaaacgct tgtcgttgat cgtgtaatat    23100
gggctatcgg ccgtggacca aatgtagaca tgggacttga aaataccgat attgttttaa    23160
atgataaaga ttatatcaaa acagatgaat ttgagaatac ttctgtagat ggcgtgtatg    23220
ctattggaga tgttaatggg aaaattgcct tgacaccggt agcaattgca gcaggtcgtc    23280
```

```
gcttatcaga aagactttt  aatcataaag ataacgaaaa attagattac cataatgtac  23340
cttcagttat tttactcac  cctgtaattg ggacggtagg actttcagaa gcagcagcta  23400
tcgagcaatt tggaaaagat aatatcaaag tctatacatc aactttacc  tctatgtata  23460
cggctgttac cagtaatcgc caagcagtta agatgaagct cataaccta  ggaaaagagg  23520
aaaaagttat tgggcttcat ggtgttggtt atggtattga tgaaatgatt caaggttttt  23580
cagttgctat caaaatgggg gctactaaag cagactttga tgatactgtt gctattcacc  23640
caactggatc tgaggaattt gttacaatgc gctaacgcta tcaaagaata caaaaaaagc  23700
tagggaacct agctttttta aggtgttgtt gtattttcaa tagttgaggt atcggtagta  23760
gtattatttg tttgatcatt gttagtacta gatgatgttt gatcgttatt ggcagcagaa  23820
tttgaactgc tactcggagt actactagca gaggaattt  ctagtgtttg gctggatgat  23880
gcccttgtct catctttttc agtagaaact tggttactag aattttgtcc actttctctt  23940
ataatgacgg ttttgaagt  agaagaatca gtcttactag agtctttgtg attattaatc  24000
gcattagtaa tagtaataga gg                                           24022
2
30
```